United States Patent [19]

Kettner et al.

[11] Patent Number: 5,187,157
[45] Date of Patent: Feb. 16, 1993

[54] PEPTIDE BORONIC ACID INHIBITORS OF TRYPSIN-LIKE PROTEASES

[75] Inventors: Charles A. Kettner; Ashokkumar B. Shenvi, both of Wilmington, Del.

[73] Assignee: Du Pont Merck Pharmaceutical Company, Wilmington, Del.

[21] Appl. No.: 178,368

[22] Filed: Apr. 6, 1988

Related U.S. Application Data

[63] Continuation-in-part of Ser. No. 59,670, Jun. 5, 1987, abandoned.

[51] Int. Cl.$^5$ .................. A61K 37/02; C07K 5/06; C07K 5/08; C07K 5/10
[52] U.S. Cl. .................. 514/18; 514/19; 514/20; 530/330; 530/331; 548/110; 548/405; 562/7
[58] Field of Search ............ 514/64, 18, 19, 20; 548/110, 405; 562/7; 530/330, 331

[56] References Cited

U.S. PATENT DOCUMENTS

| | | | |
|---|---|---|---|
| 4,318,904 | 3/1982 | Shaw et al. | 424/177 |
| 4,499,082 | 2/1985 | Shenvi et al. | 514/2 |
| 4,537,773 | 8/1985 | Shenvi | 514/63 |

FOREIGN PATENT DOCUMENTS 0181267  5/1986  European Pat. Off. .

OTHER PUBLICATIONS

Phillipp et al., Federation Proceedings, 46(6): 2223, abstract #1737 (1987).
Koehler et al., Biochemistry 10: 2477-2483 (1971).
Matteson et al., J. Am. Chem. Soc. 103: 5241-5242 (1981).
Lienhard, in Enzyme Inhibitors as Drugs, Sandler, ed., University Park Press, Baltimore pp. 43-51 (1980).
Kinder et al., J. Med. Chem. 28: 1917-1925 (1985).
Baumgarten et al., J. Immun. 137: 977-982 (1986).
Wachtfogel et al., Blood 67: 1731-1737 (1986).
Markwardt, TIPS 153-157 (1980).
Green et al., Thromb. Res. 37: 145-153 (1985).
Kettner et al., in Methods in Enzymology, Lorand, ed., Academic Press, New York, 80: 826-842 (1981).
Bajusz et al., Int. J. Peptide Protein Res. 12: 217-221 (1979).
Tremoli et al., Thromb. Res. 23: 549-553 (1981).
Kikumoto et al., Biochemistry 23: 85-90 (1984).
Kaiser et al., Thromb. Res. 43: 613-620 (1986).
Sturzebecher et al., Thromb. Res. 29: 635-642 (1983).
D. S. Matteson et al., Organometallics 3, 1284-1288 (1984).
D. S. Matteson et al., J. Am. Chem. Soc. 103, 5242-5245 (1981).
D. K. Kinder and J. A. Katzenellenbogen, J. Med. Chem. 28, 1917-1925. (1985).

Primary Examiner—Mary C. Lee
Assistant Examiner—Michael G. Ambrose
Attorney, Agent, or Firm—Blair Q. Ferguson; Suzanne E. Miller

[57] ABSTRACT

Peptides comprising C-terminal boronic acid derivatives of lysine, ornithine, and arginine, homoarginine and corresponding isothiouronium analogs thereof, are reversible inhibitors of trypsin-like serine proteases such as thrombin, plasma kallikrein and plasmin.

51 Claims, 1 Drawing Sheet

PEPTIDE BORONIC ACID INHIBITORS OF TRYPSIN-LIKE PROTEASES

BACKGROUND OF THE INVENTION

1. Field of the Invention

The present invention relates generally to C-terminal alpha-aminoboronic acid derivatives of lysine, ornithine, and arginine, homoarginine and corresponding isothiouronium analogs thereof, and their use as inhibitors of trypsin-like serine proteases such as thrombin, plasma kallikrein and plasmin.

2. Background

The activity of many biological systems is mediated by hydrolytic or proteolytic enzymes that cleave precurser proteins at specific locations. Four classes of these enzymes exist, metallo, thiol, acid and serine proteases. Systems such as blood coagulation, fibrinolysis, complement, and kallikrein-kinin are all regulated by a subclass of serine proteases, the trypsin-like proteases, a group of enzymes that have a primary specificity for arginyl or lysyl residues.

Within each class, the mechanism of action and the active site residues of the enzymes as well as their susceptibility to class specific inhibitors are similar. The ability of a compound to effectively inhibit a particular protease or a particular subclass of proteases, however, is strongly dependent upon the structure and composition of the compound.

A great deal of research has been done in the area of protease inhibition, and a number of researchers in this area have experimented with boron-containing inhibitors.

Shenvi, U.S. Pat. No. 4,537,773 (1985), for example, reports that alpha-aminoboronic acid analogs of amino acids containing aliphatic and aromatic alkyl side chains are effective inhibitors of metalloenzymes. In addition, Shenvi et al., U.S. Pat. No. 4,499,082 (1985) disclose that alpha-aminoboronic acids incorporated into peptides inhibit serine proteases whose primary specificity requirements are met by neutral side chains, such as pancreatic and leukocyte elastase, chymotrypsin, and cathepsin G. This latter patent discloses tetrapeptides comprising C-terminal alpha-aminoboronic acid residues as potent, reversible inhibitors of such proteolytic enzymes. The peptides disclosed, however, did not include C-terminal alpha-aminoboronic acid residues of lysine, ornithine, arginine, homoarginine or any corresponding isothiouronium salts.

Koehler et al., Biochemistry 10: 2477 (1971) report that 2-phenyl-ethaneboronic acid is an inhibitor of chymotrypsin. Matteson et al., J. Am. Chem. Soc. 103: 5241 (1981), describe the synthesis of (R)-1-acetamido-2-phenylethane boronic acid and its use as an inhibitor of chymotrypsin. The authors show a $K_i$ of 4 $\mu$M.

Lienhard in *Enzyme Inhibitors as Drugs*, Sandler, ed., University Park Press, Baltimore pp.43–51 (1980) speculates that peptide analogs of alpha-aminoboronic acids will be potent inhibitors of serine and thiol proteases.

Additional disclosures include those of Kinder et al., J. Med. Chem. 28: 1917–1925 (1985), which describes the N-acyl and dipeptide boronic acids and difluoroborane analogs of phenylalanine, phenylglycine, alanine, valine, and isoleucine, and Matteson, Organometallics 3: 1284–1288 (1984) which describes the synthesis of alpha-amido gama-substituted boronic esters. The latter authors state that these compounds were prepared as possible precursors to boronic acid analogs of arginine and proline.

Trypsin-like proteases are extremely important in controlling a number of physiological processes. For a discussion of such activity, see "Proteases and Biological Control", Reich, Rifkin and Shaw eds., Cold Spring Harbor Press (1975). Thrombin, one type of trypsin-like protease, has a clear and decisive role in the blood coagulation process. Blood coagulation may occur through either of two cascades of zymogen activations. The last protease in each of these pathways is thrombin, which acts to hydrolyze fibrinogen to form fibrin, which in turn aggregates to form a blood clot. This thrombin catalyzed hydrolysis is essential to the blood coagulation process.

Plasma kallikrein, another trypsin-like protease, is also involved in the blood coagulation process, specifically in the initiation of one of the blood coagulation pathways. Also, kallikrein acts on kininogen to liberate the nonapeptide, bradykinin. Bradykinin is a hypotensive peptide that is associated with pain. In addition, kallikrein is thought to have other biological functions. Recent information suggests that plasma kallikrein is involved in inflammation. Baumgarten et al., J. Immun. 137: 977–982 (1986), for example, report elevated levels of kinin and kallikrein in allergic individuals challenged with allergen. Wachtfogel et al., Blood 67: 1731–1737 (1986) report that plasma kallikrein aggregates human neutrophils and releases neutrophil elastase. The release of elastase and accompanying elastase-mediated tissue destruction are events associated with the process of inflammation.

The design of specific inhibitors of trypsin-like enzymes to control biological processes is not a new concept. Particular efforts have been made in the preparation of inhibitors of thrombin to replace heparin in treatment of thrombosis without the side effects associated with heparin therapy, see Markwardt TIPS 153–157 (1980) and Green et al., Thromb. Res. 37: 145–153 (1985). Highly effective peptide chloromethyl ketones have been prepared for a number of trypsin-like proteases by Kettner et al., Methods in Enzymology 80: 826–842) (1981). One example, H-(D)Phe-Pro-ArgCH$_2$Cl, is highly effective in the inhibition of thrombin ($K_i$=37 nM), and, as shown by Shaw et al., U.S. Pat. No. 4,318,904 (1982), is effective in the prevention of coronary thrombosis in a rabbit model. Similarly, Bajusz et al., Int. J. Peptide Protein Res. 12: 217–221 (1979) report the peptide aldehyde, H-(D)Phe-Pro-Arg-H, is an effective inhibitor of thrombin ($K_i$=75 nM) and Tremoli et al., Thromb. Res. 23: 549–553 (1981), report that a related compound, Boc-(D)Phe-Pro-Arg-H, reduces the size of venous thrombosis in rats.

Substituted arginine amides composed of secondary amines have also been shown to be effective inhibitors of thrombin. Kikumoto et al., Biochemistry 23: 85–90 (1984) report that (2R,4R)-4-methyl-1[N$^2$-{(3-methyl-1,2,3,4-tetrahydro-8-quinolinyl)sulfonyl}-L-arginyl]-2-piperidinecarboxylic acid is an inhibitor of thrombin ($K_i$=19 nM). As reported by Green et al., Thromb. Res. 37: 145–153 (1985), this inhibitor increases the prothrombin times of plasma in vitro blood coagulation assays 2-fold at 1 $\mu$M, and it is claimed as a fibrinolytic enhancing agent to be used in combination with tissue plasminogen activator Yoshikuni et al, European Patent Application 0,181,267 (1986). Finally, Sturzebecher et al., Thromb. Res. 29: 635–642 (1983) and Kaiser et al., Thromb. Res. 43: 613-620 (1986) report that N-alpha-(2-naphthylsulfonyl-glycyl)-4-amidinophenyl-alanine piperidide is the most effective known inhibitor of thrombin ($K_i = 6$ nM), and demonstrate that is in vivo efficacy in mice and rats.

Despite the foregoing, new and better classes of inhibitors of thrombin and other trypsin-like enzymes are needed to provide potentially valuable therapeutic agents for treatment of blood coagulation disorders, inflammation and other mammalian ailments. The present invention is directed to this end.

SUMMARY OF THE INVENTION
The present invention provides compounds of the formula

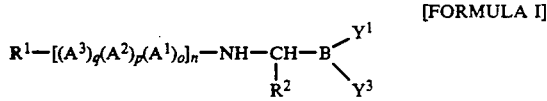
[FORMULA I]

wherein $Y^1$ and $Y^2$, independently, are —OH or F or, taken together, form a moiety derived from a dihydroxy compound having at least two hydroxy groups separated by at least two connecting atoms in a chain or ring, said chain or ring comprising 1 to about 20 carbon atoms and, optionally, a heteroatom which can be N, S, or O;

$R^2$ is a substituted alkyl selected from the group consisting of —$(CH_2)_z$—X, —$CH(CH_3)$—$(CH_2)_2$—X, —$CH_2$—$CH(CH_3)$—$CH_2$—X, —$(CH_2)_2$—$CH(CH_3)$—X, and —$(CH_2)_2$—$CH(CH_3)_2$—X, where X is —$NH_2$, —NH—C(NH)—$NH_2$ or —S—C(NH)—$NH_2$, and z is 3 to 5;

n, o, p, and q are, independently, either 1 or 0;

$A^1$, $A^2$ and $A^3$, independently, are amino acids of L- or D-configuration selected from the group consisting of Ala, Arg, Asn, Asp, Cys, Gln, Glu, Gly, His, Ile, Leu, Lys, Met, Phe, Pro, Ser, Thr, Trp, Tyr and Val; and $R^1$ is a peptide comprised of 1 to about 20 amino acids, an acyl or a sulfonyl group comprised of 1 to about 20 carbon atoms, H, or an N-terminal protecting group;

or a physiologically acceptable salt thereof.

The invention also provides compositions comprising one or more of the foregoing Formula I compounds, and methods of using such compounds or compositions in the inhibition of trypsin-like serine proteases, such as thrombin and plasma kallikrein, and in the treatment of aberrant physiological conditions, such as those involving blood coagulation disorders and inflammation, which are mediated by trypsin-like proteases.

Further, two classes of intermediates to the foregoing compounds are provided. The first such class of intermediates includes compounds of the formula

[FORMULA II]

wherein $Y^3$ is a moiety derived from a dihydroxy compound having at least two hydroxy groups separated by at least two connecting atoms in a chain or ring, said chain or ring comprising 1 to about 20 carbon atoms;

$R^3$ is a substituted alkyl selected from the group consisting of —$(CH_2)_z$—$W^1$, —$CH(CH_3)$—$(CH_2)_2$—$W^1$, —$CH_2$—$CH(CH_3)$—$CH_2$—$W^1$, —$(CH_2)_2$—$CH(CH_3)$—$W^1$ and —$(CH_2)_2$—$CH(CH_3)_2$—$W^1$;

W and $W^1$, independently, are Cl or Br; and
z is 3 to 5.

The second class of intermediates includes compounds of the formula

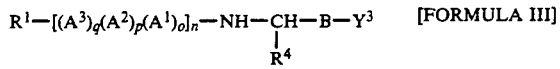
[FORMULA III]

wherein $A^1$, $A^2$, $A^3$, $Y^3$, $R^1$, n, o, p and q are as previously defined;

$R^4$ is a substituted alkyl selected from the group consisting of —$(CH_2)_z$—$W^2$, —$CH(CH_3)$—$(CH_2)_2$—$W^2$, —$CH_2$—$CH(CH_3)$—$CH_2$—$W^2$, —$(CH_2)_2$—$CH(CH_3)$—$W^2$, and —$(CH_2)_2$—$CH(CH_3)_2$—$W^2$;

$W^2$ is Cl, Br or $N_3$ and
z is 3 to 5.

DETAILED DESCRIPTION OF THE INVENTION

Figure 1:
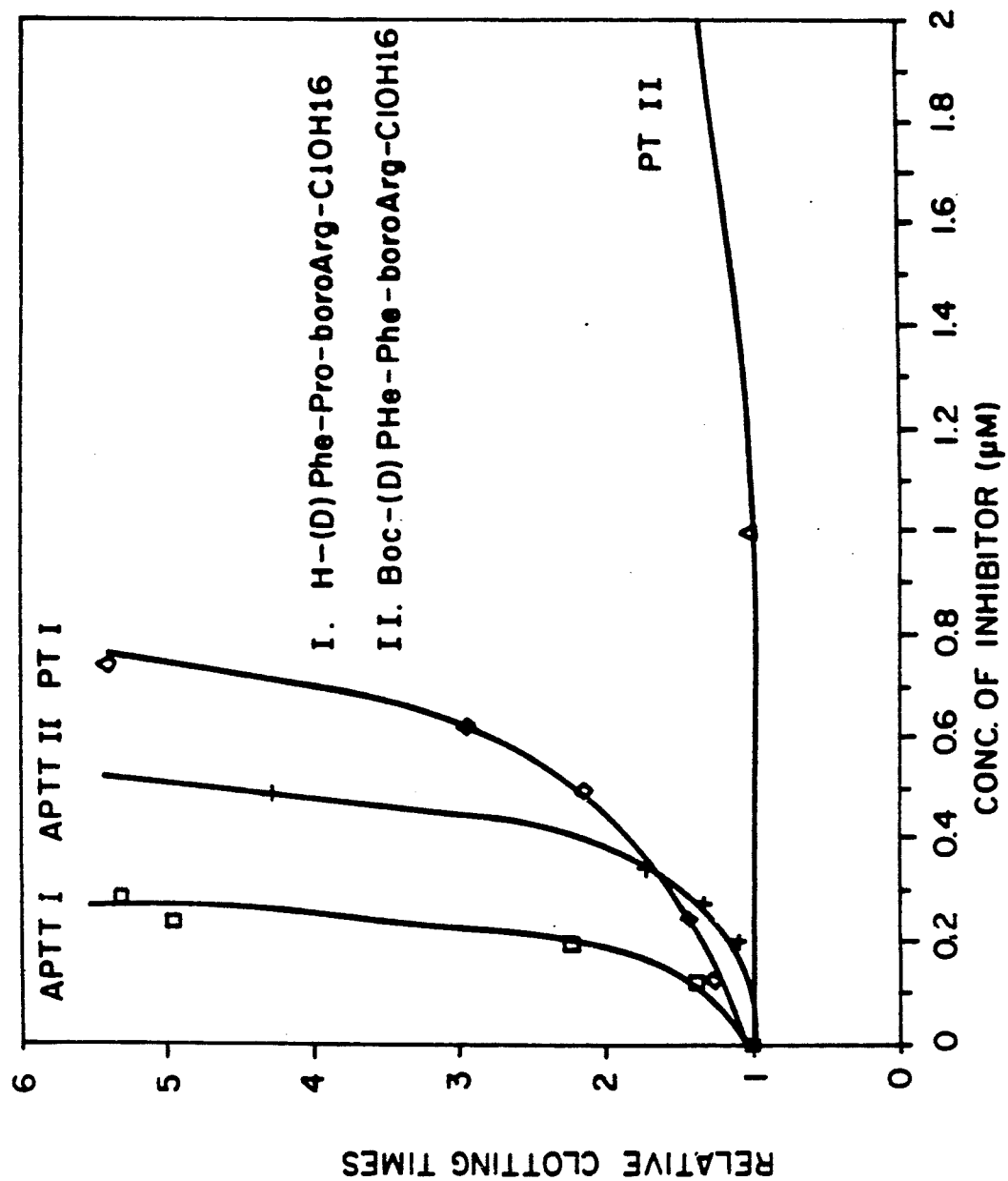
FIG. 1 shows a plot of relative clotting times versus inhibitor concentration for two inhibitors of the invention, H-(D)Phe-Pro-boroArg-$C_{10}H_{16}$ and Boc-(D)Phe-Phe-boroArg-$C_{10}H_{16}$. The data for FIG. 1 was obtained from Tables 3 and 4. Relative clotting time is the activated partial thromboplastin times (APTT) or the prothrombin times (PT), as the case may be, in the presence of inhibitor, divided by the APTT or respectively, in the absence of the inhibitor. The inhibitor concentration is shown in micro molar.

The principal compounds of the present invention, the Formula I compound, are N-acyl and peptide derivatives of alpha-aminoboronic acids in which the C-terminal residue consists of lysine, ornithine, and arginine, homoarginine and corresponding isothiouronium analogs thereof. These compounds are characterized by their potency as inhibitors of certain trypsin-like proteolytic enzymes, notably human thrombin, plasma kallikrein and plasmin.

The acid terminal boron of the present compounds can optionally be in the form of an unprotected boronic acid, that is, where $Y^1$ and $Y^2$ each are —OH, or borane difluoride, that is, where $Y^1$ and $Y^2$ each are —F, or combinations thereof. Alternatively, the terminal boron can be protected with a wide variety of protecting groups wherein $Y^1$ and $Y^2$ are taken together (—$Y^1$—$Y^2$) to form a moiety.

Suitable protecting groups wherein $Y^1$ and $Y^2$ are —$Y^1$—$Y^2$—include moieties derived from compounds, principally diols, having at least two hydroxy groups separated by at least two connecting atoms in a chain or ring. The term chain denotes both a branched or unbranched moiety. The chain or ring is comprised of 1 to about 20 carbon atoms and, optionally, and may include a heteroatom which can be N, s or P. Contemplated compounds within the foregoing description include, for example, pinanediol, pinacol, perfluoropinacol, ethylene glycol, diethylene glycol, catechol, 1,2-cyclohexanediol, 1,3-propanediol, 2,3-butanediol, 1,2-butanediol, 1,4-butanediol, glycerol, diethanolamine and other amino alcohols, and other equivalents apparent to those skilled in the art.

As used throughout the specification, the following abbreviations for amino acid residues or amino acids apply:

Ala=L-alanine
Arg=L-arginine
Asn=L-asparagine
Asp=L-aspartic acid
Cys=L-cysteine
Gln=L-glutamine
Glu=L-glutamic acid
Gly=glycine
His=L-histidine
Ile=L-isoleucine
Leu=L-leucine
Lys=L-lysine
Met=L-methionine
Phe=L-phenylalanine
Pro=L-proline
Ser=L-serine
Thr=L-threonine
Trp=L-tryptophan
Tyr=L-tyrosine
Val=L-valine Where prefixed by a "D", the foregoing abbreviations indicate an amino acid of D-configuration. Where prefixed by a "D or L", the foregoing abbreviations indicate that the amino acid can be of either the D- or the L-configuration. "N-terminal protecting group," as used herein, refers to various amino-terminal protecting groups employed in peptide synthesis. Examples of suitable groups include acyl protecting groups, for example, formyl, acetyl (Ac), benzoyl (Bz), trifluoroacetyl, and methoxysuccinyl (MeOSuc); aromatic urethane protecting groups, for example, benzyloxycarbonyl (Z); and aliphatic urethane protecting groups, for example, tert-butoxycarbonyl (Boc) or adamantyloxycarbonyl. Gross and Mienhoffer, eds., The Peptides, Vol. 3: 3–88 (1981), Academic Press, New York 1981, disclose numerous suitable amine protecting groups. The following represent preferred N-terminal protecting groups $R^1$:

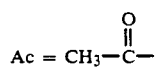

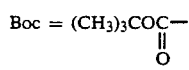

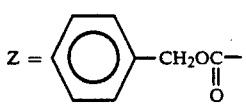

Compounds of the invention having side-chain amino groups, for example, where $A^1$, $A^2$ or $A^3$ are Lys or Arg, can optionally contain suitable N-terminal protecting groups attached to the side chains; similarly, amino acid residues having acidic or hydroxy side chains can be protected in the form of t-butyl, benzyl or other suitable esters or ethers.

As noted previously, R: refers to an alkyl group comprised of 3 to 5 carbons attached to an amino, guanidino, or isothiouronium group. Preferrably, the $R^2$ is $-(CH_2)_z-X$. A more preferred value of $R^2$ is $-(CH_2)_z-X$ where z is 3 to 4. Examples of more preferred values of $R^2$ include 3-guanidino-propyl, 3-amino-propyl, and 4-amino-butyl. Most preferred is 3-guanidino-propyl.

Abbreviations and terms prefixed by "boro-" indicate amino acids of Formula I wherein the terminal carboxyl group $-CO_2H$ has been replaced by a boronic functionality

Thus, "boroarginine" or "boroArg-" refers to boronic acid analogs of arginine; "borolysine" or "boroLys-" refers to boronic acid analogs of lysine; and "boroornithine" or "boroOrn-" refers to boronic acid analog of ornithine. The prefix "homo", as in "homoboroarginine" or "homoboroArg-", refers to boroarginine analogs in which the side chain has an additional methylene group. "Irg" refers to the isothiouronium analog of arginine or homoarginine in which the thiouronium group, $-S-C(NH)NH_2$, replaces the guanidino group, $-NH-C(NH)-NH_2$, and "boroIrg-" or "borohomoIrg-" is the abbreviation for the corresponding boronic acid analog.

In naming compounds of the invention, $Y^1$ and $Y^2$ are simplified by the suffix "—F" for the difluoroboranes ($Y^1=Y^2=-F$), "—OH" for the unprotected boronic acids ($Y^1=Y^2=-OH$), "—$C_6H_{12}$" for the pinacol esters ($Y^1$ and $Y^2$, taken together, are $-O_2C_6H_{12}$), and "—$C_{10}H_{16}$" for the pinanediol esters ($Y^1$ and $Y^2$, taken together, are $-O_2-C_{10}H_{16}$).

The present invention also contemplates physiologically acceptable salts of Formula I. These salts include acid addition salts, for example, salts of benzene sulfonic acid (BSA), hydrochloric acid (HCl), hydrobromic acid (HBr), acetic acid, trifluoroacetic acid (TFA), succinic acid, citric acid, or other suitable acid addition salts. When employed in naming compounds of the present invention, these salts shall be introduced in the compound name by a ".".

Contemplated classes of compounds within the scope of the present invention include the following amino acids of the D- or L-configuration. A first class includes compounds wherein $A^1$ is Ala, Pro, Gly, Val, Leu, Ile or Met, that is, an amino acid having a neutral side chain. A second class includes compounds wherein $A^1$ is Phe, Trp or Tyr, that is, an amino acid having an aromatic side chain. A third class includes compounds wherein $A^1$ is Lys or Arg, that is, a basic amino acid, and a fourth class includes compounds wherein $A^1$ is Ser or Thr, that is, an amino acid with a hydroxy side chain. Finally, a fifth class includes compounds wherein $A^1$ is Asp, Glu, Asn or Gln, that is, an amino acid with an acidic or a carboxamido side an amino acid with an acidic or a carboxamido side chain. Preferable values of A substituents include Lys, Phe, Pro, Ala, Leu, Gly, Glu, Val, Thr, Ile, Met, Tyr, Trp, Arg, Asp, Asn and Gln. One preferable class of such substituents includes Lys, Phe, Pro, Ala, Leu, Gly, Glu, Val and Thr.

The foregoing principal classes include subclasses corresponding to preferred values of $R^2$, and these subclasses are further subtended into groups defined by preferred values for $A^2$ and for N-terminal protecting group $R^1$.

Preferred values for $A^2$ include all amino acids having a D-configuration, most preferably (D)Phe. Other preferrable values for $A^2$ are (D or L) Phe, (D or L) Ala, (D or L) Leu, (D or L) Pro, (D or L) Glu and (D or L) Gly. Another class of $A^2$ substituents includes (L) Glu and (D) Val.

Preferrably, the Formula I compounds have a total of two to four amino acid substituents, including the boro amino acid analog. A three amino acid compound which has Pro in the $A^1$ position and boroArg as the boro amino acid analog, such as

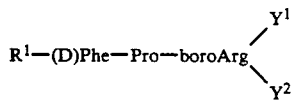

are particularily suited as inhibitors of thrombin, having an IC 50 of significantly less than 5 nM.

Obvious equivalents of the foregoing compounds include compounds comprising less common or modified amino acids, for example, norleucine, hydroxyproline, pyroglutamic acid or other derivatives, including residues with side chain protecting groups, capable of incorporation into the alpha-aminoboronic acid peptides of the present invention.

Specific compounds within the scope of the invention, named in accordance with the conventions described above, include the following examples:

Ac-(D,L)Phe-boroArg-$C_{10}H_{16}$.BSA
Ac-Phe-boroOrn-$C_{10}H_{16}$.BSA
Ac-Phe boroArg-$C_{10}H_{16}$.HCl
H-(D)Phe-Pro-boroIrg-$C_{10}H_{16}$.HBr.HCl
Boc-(D)Phe-Pro-boroIrg-$C_{10}H_{16}$. HBr
Ac-Phe-boroIrg-$C_{10}H_{16}$.HBr
Ac-Ala-Lys(Boc)-boroOrn-$C_{10}H_{16}$.BSA
Ac-Ala-Lys(Boc)-boroIrg-$C_{10}H_{16}$.HBr
Boc-(D)Phe-Pro-boroArg-$C_{10}H_{16}$.BSA
Boc-(D)Phe-Phe-BoroIrg-$C_{10}H_{16}$.HBr
H-(D)Phe-Pro-boroArg-$C_{10}H_{16}$.HCl
Boc-(D)Phe-Phe-boroOrn-$C_{10}H_{16}$.BSA
Boc-(D)Phe-Phe-boroArg-$C_{10}H_{16}$.BSA
Ac-Ala-Lys(Boc)-boroArg-$C_{10}H_{16}$.BSA
Ac-(D)Phe-Pro-boroArg-$C_{10}H_{16}$.HCl
Ac-(D)Phe-Pro-boroArg-OH.HCl
Boc-Leu-Gly-Leu-Ala-boroIrg-$C_{10}H_{16}$.HBr
Boc-Leu-Gly-Leu-Ala-boroOrn-$C_{10}H_{16}$.BSA
Boc-Leu-Gly-Leu-Ala-boroArg-$C_{10}H_{16}$.BSA
Bz-Pro-Phe-boroOrn-$C_{10}H_{16}$.BSA
Bz-Pro-Phe-boroArg-$C_{16}H_{16}$.BSA
Boc-Ala-Phe-(D,L)boroIrg-$C_6H_{12}$.HBr
Bz-Glu(OBu)-Gly-boroIrg-$C_{10}H_{16}$.HBr
Bz-Glu-Gly-boroArg-$C_{10}H_{16}$.BSA
Bz-Glu(OBu)-Gly-boroOrg-$C_{10}H_{16}$.BSA
Bz-Glu(OBu)-Gly-boroArg-$C_{10}H_{16}$.BSA
Bz-Pro-Phe-boroIrg-$C_{10}H_{16}$.HBr
Z-Phe-Gly-Gly-boroIrg-$C_{10}H_{16}$.HBr
Boc-Ala-Phe-(D,L)borohomoIrg-$C_6H_{12}$.HBr
Bz-Pro-Phe-boroArg-OH.HCl
Bz-Pro-Phe-boroArg-F
H-(D)Phe-Pro-boroArg-$C_{10}H_{16}$.2HCl
H-(D)Phe-Phe-boroArg-$C_{10}H_{16}$.2HCl
Ac-Ala-Lys-boroArg-$C_{10}H_{16}$.2HCl
H-Leu-Gly-Leu-Ala-boroArg-$C_{10}H_{16}$.HCl.BSA
Boc-Ala-Phe-(D,L)boroLys-$C_6H_{12}$.HCl
H-Ala-Phe-(D,L)boroLys-$C_6H_{12}$.2HCl
Boc-(D)Val-Leu-boroLys-$C_6H_{12}$.HCl
Ac-Phe-boroLys-$C_6H_{12}$.HCl
Bz-Glu-Gly-boroArg-$C_{10}H_{16}$.BSA
H-(D)Phe-Phe-boroIrg-$C_{10}H_{16}$.2HBr
H-Leu-Gly-Leu-Ala-boroIrg-$C_{10}H_{16}$.2HBr
H-Ala-Phe-(D,L)boroIrg-$C_6H_{12}$.2HBr
Bz-Glu-Gly-boroIrg-$C_{10}H_{16}$.HBr
H-Ala-Phe-(D,L)boroHomoIrg-$C_6H_{12}$.2HBr
Ac-Ala-Lys-boroIrg-$C_{10}H_{16}$.2HBr
Bz-boroIrg-$C_6H_{12}$.HBr
Bz-boroOrn-$C_6H_{12}$.BSA
Bz-boroArg-$C_6H_{12}$.BSA
Ac-Leu-Thr(OBu)-boroOrn-$C_{10}H_{16}$.BSA
Ac-Leu-Thr(OBu)boroArg-$C_{10}H_{16}$.BSA
Ac-Leu-Thr-boroArg-$C_{10}H_{16}$.BSA
Ac-Lys(Boc)-Pro-boroOrn-$C_{10}H_{16}$.BSA
Ac-Lys(Boc)-Pro-boroArg-$C_{10}H_{16}$.BSA
Ac-Lys-Pro-boroArg-$C_{10}H_{16}$.BSA
Ac-Ala-Glu(OBu)-boroOrn-$C_{10}H_{16}$.BSA
Ac-Ala-Glu(OBu)-boroArg-$C_{10}H_{16}$.BSA
Ac-Ala-Glu-boroArg-$C_6H_{16}$.BSA
Boc-Val-Val-boroLys-$C_6H_{12}$.BSA
H-Val-Val-boroLys-$C_6H_{12}$.BSA.TFA
Boc-(D)Phe-Phe-boroLys-$C_6H_{12}$.BSA
H-(D)Phe-Phe-boroLys-$C_6H_{12}$.BSA.TFA
Boc-Glu-Phe-boroLys-$C_6H_{12}$.BSA
PyroGlu-Phe-boroLys-$C_6H_{12}$.BSA The invention also provides compositions and methods for inhibiting trypsin-like serine proteases, including but not limited to thrombin, plasma kallikrein and plasmin, and for treating aberrant physiological conditions, including but not limited to blood coagulation and inflammation in mammals. The compositions of the present invention comprise an effective amount of a compound of Formula I and a physiologically acceptable carrier or diluent. In practicing the method of the invention, the compounds or compositions can be used alone or in combination with one another, or in combination with other therapeutic agents. They can be administered orally, parenterally, intravenously, subcutaneously, intramuscularly, colonically, rectally, nasally or intraperitoneally in a variety of dosage forms. The useful dosage to be administered and the mode of administration will vary depending upon the age, weight and mammal treated, and the particular compounds employed. Typically, therapy is initiated at lower dosage levels with dosage being increased until the desired effect is acheived.

The present invention further contemplates two classes of critical intermediates to compounds of Formula I, the compounds of Formulas II and III. The Formula II intermediates includes compounds of the formula

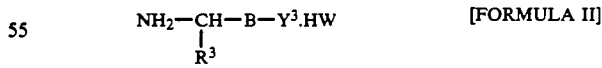

wherein $Y^3$ is a moiety derived from a dihydroxy compound having at least two hydroxy groups separated by at least two connecting atoms in a chain or ring, said chain or ring comprising 1 to about 20 carbon atoms;

$R^3$ is a substituted alkyl selected from the group consisting of $-(CH_2)_z-W^1$, $-CH(CH_3)-(CH_2)_2-W^1$, $-CH_2-CH(CH_3)-CH_2-W^1$, $-(CH_2)_2-CH(CH_3)-W^1$ and $-(CH_2)_2-CH(CH_3)_2-W^1$;

W and $W^1$, independently, are Cl or Br; and z is 3 to 5.

A particularly preferred compound of Formula II is one wherein R is —$(CH_2)_z$—$W^1$ and z is 3 to 4.

A second class of intermediates includes compounds of the formula $$R^1-[(A^3)_q(A^2)_p(A^1)_o]_n-NH-\underset{R^4}{CH}-B-Y^3 \quad \text{[FORMULA III]}$$

wherein $A^1$, $A^2$, $A^3$, $Y^3$, $R^1$, n, o, p and q are as previously defined;

$R^4$ is a substituted alkyl selected from the group consisting of —$(CH_2)_z$—$W^2$, —$CH(CH_3)$—$(CH_2)_2$—$W^2$, —$CH_2$—$CH(CH_3)$—$CH_2$—$W^2$, —$(CH_2)_2$—$CH(CH_3)$—$W^2$, and —$(CH_2)_2$—$CH(CH_3)_2$—$W^2$;

$W^2$ is Cl, Br or $N_3$ and z is 3 to 5.

Contemplated classes of compounds within the scope of Formula III are as described for the analogous Formula I compounds A particularly preferred compound of Formula III is one wherein R is —$(CH_2)_z$—$W^2$ and z is 3 to 4.

Preparation of Inhibitors

Temperatures are in °C. The numbered compounds shown in the schematic entitled "Synthesis Scheme", illustrated below, are referred to in the text according to their respective numbers. "NMR", as used herein, signifies proton nuclear magnetic resonance.

SYNTHESIS SCHEME

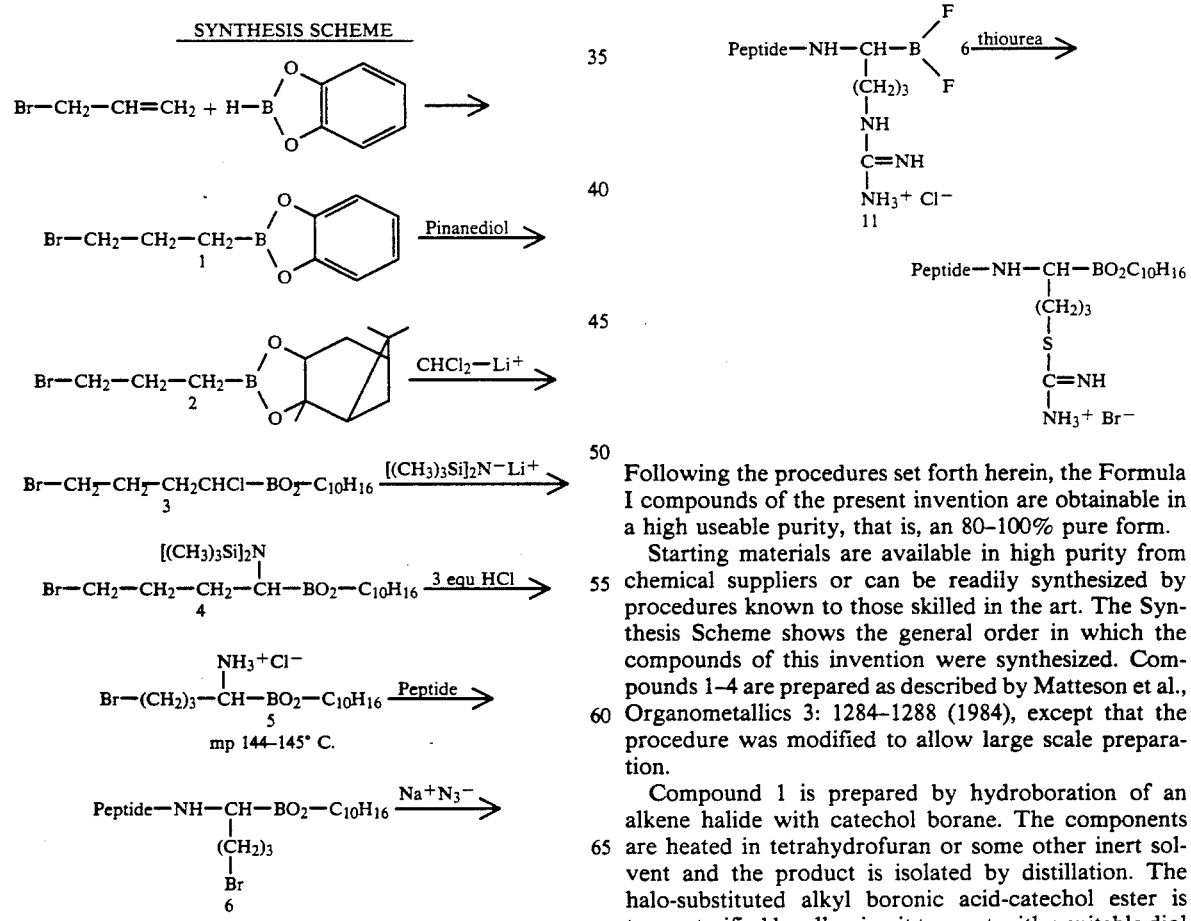

Following the procedures set forth herein, the Formula I compounds of the present invention are obtainable in a high useable purity, that is, an 80–100% pure form.

Starting materials are available in high purity from chemical suppliers or can be readily synthesized by procedures known to those skilled in the art. The Synthesis Scheme shows the general order in which the compounds of this invention were synthesized. Compounds 1–4 are prepared as described by Matteson et al., Organometallics 3: 1284–1288 (1984), except that the procedure was modified to allow large scale preparation.

Compound 1 is prepared by hydroboration of an alkene halide with catechol borane. The components are heated in tetrahydrofuran or some other inert solvent and the product is isolated by distillation. The halo-substituted alkyl boronic acid-catechol ester is transesterified by allowing it to react with a suitable diol (alpha-pinanediol, pinacol, 2,3-butandiol, etc) in tetrahydrofuran. (+)-Alpha-pinanediol is preferred in view of the observations in Matteson et al., J. Am. Chem. Soc. 103: 5241 (1981) that steric restraints in the molecule allow the stereo specific addition of the —CHCl— group in formation of Compound 3 and the subsequent introduction of an amino group in the "L" configuration. Structures 3-9 in the Synthesis Scheme are shown with the pinanediol protecting group. For large scale preparations, the removal of catechol, a product of the esterification reaction, is achieved by crystallization from hexane, a solvent in which catechol has limited solubility. Compound 2 is then purified either by chromatography on silica gel, by distillation, or is used without additional purification. Compound 2, as the pinanediol ester is obtained in close to analytical purity by the removal of solvent. Additional purification can be achieved by silica gel chromotography. For the pinacol ester of Compound 2, final purification by distillation is preferred.

Compound 3 is prepared by the homologation of 2 using $CHCl_2^-Li^+$. This reagent is made by treating methylene chloride with n-butyllithium in tetrahydrofuran at $-100°$. To Compound 2 is added 0.65 equivalents of zinc chloride at $-100°$. The mixture is allowed to slowly warm to room temperature and is stirred over night. Compound 3 is obtained after evaporating solvent, then dissolving the residue in hexane, followed by washing the organic phase with water, drying it with magnesium sulfate, and finally evaporating the hexane. Compound 3 is used without further purification when it is protected as the pinanediol ester and alternately, it can be distilled when it is protected as a pinacol ester.

Compound 4 is prepared by treating the alpha-chloro-substituted boronic acid ester, Compound 3, with $[(CH_3)_3Si]_2N^-Li^+$. Hexamethyldisilazane is dissolved in tetrahydrofuran and an equivalent of n-butyllithium is added at 78°. The mixture is allowed to warm to room temperature and then, after recooling to $-78°$, an equivalent of 3 is added in tetrahydrofuran. The mixture is allowed to slowly come to room temperature and to stir over night. The alpha-bis[trimethylsilane]-protected amine is isolated by evaporating solvent and adding hexane under anhydrous conditions. Insoluble residue is removed by filtration under a nitrogen blanket yielding a hexane solution of Compound 4.

Compound 5 is obtained by cooling the hexane solution of Compound 4 to $-78°$ and adding three equivalents of hydrogen chloride. The solution is slowly allowed to warm to room temperature and is stirred for 1.5-2 h. Compound 5 is then isolated by filtration and is purified further by dissolving in chloroform and removing insoluble material. Compound 5 is obtained as a white crystalline solid by removing the chloroform by evaporation and crystallizing the residue for ethyl acetate.

The above process of converting Compound 3 to Compound 5 surprisingly results in analytically pure preparations of Compound 5 which then allows Compound 6 to be obtained without the difficulty normally encountered in coupling heterogenous material. The art teaches or strongly suggests that Compound 4 has to be purified prior to conversion to Compound 5 in order to obtain pure samples. The only known procedure for the preparation of pure alpha-aminoboronic acids is that disclosed in Shenvi U.S. Pat. No. 4,537,773 and used in Shenvi et al., U.S. Pat. No. 4,499,082. In the Shenvi et al. disclosure, compounds analgous to Compound 4, except that they have aromatic and alkyl side chains, are purified by distillation. Compound 4 is unstable to the Shenvi et al. distillation and an altered product is obtained.

Compound 6, the N-acyl or N-peptidyl form of Compound 5, can be prepared by two different routes. The first is a modification of the procedure described by Matteson et al., Organometallics 3: 1284-1288 (1984) in which Compound 4, prepared in situ (without evaporation of solvent and removal of salts by filtration), is treated with an equivalent of acetic acid and an excess of acetic anhydride to yield N—Acetyl—N-H—CH[(CH$_2$)$_3$Br]BO$_2$-pinanediol. This method is applicable to the coupling of highly reactive acid chloride of N-Acetyl-phenylalanine (Ac-Phe-Cl) with the modification that prior treatment with acetic acid is omitted. When acetic acid is added in conjunction with Ac-Phe-Cl, extremely low yield are obtained which appear to be due to the formation of the a mixed anhydride of Ac-Phe and acetic acid and the subsequent chemically preferred coupling which results in N—acetyl—NH—CH[(CH$_2$)$_3$Br]BO$_2$-pinacol. Application of the mixed anhydride procedure to the preparation of Compound 6 resulted in low yields of the desired product and extensive problems in purification. Thus, it appears that this method is applicable to the coupling of alkyl, aryl, and N-protected amino acids to Compound 4 by using the acid chloride method. However, it should be noted that there are limitations due to the requirement of the acid chloride coupling procedure. First, the procedure is not readily applicable to peptide coupling because of side reactions such as oxazolinone formation limiting its application to a single amino acid residue. Second, an acid stable protecting group is required due to excess HCl generated during formation of the acid chloride. Finally, racemization of amino acid residue is inherent in the procedure.

The second method for the preparation of Compound 6 is the coupling of an acyl group or N-protected peptide with suitable side chain protection to Compound 5. This method is clearly superior to the first since it is sufficiently versatile to allow the synthesis of any peptide within the limits normally encountered during peptide synthesis such as insufficient solubility. Acid chlorides or other active forms of acyl groups can be coupled. For peptides, the mixed anhydride procedure of Anderson et al., J. Am. Chem. Soc. 89: 5012 (1967) is preferred. The mixed anhydride of N-protected amino acids or peptides varying in length from a dipeptide to tetrapeptide with suitable side chain protecting groups is prepared by dissolving the given peptide in tetrahydrofuran and adding one equivalent of N-methylmorpholine. The solution is cooled to $-20°$ and an equivalent of isobutyl chloroformate is added. After 5 min, this mixture and one equivalent of triethylamine (or other stericly hindered base) are added to a solution of Compound 5 dissolved in either cold chloroform or tetrahydrofuran. The reaction mixture is routinely stirred one hour at $-20°$ followed by 1-2 h of stirring at room temperature. Insoluble material is removed by filtration, the solvent removed by evaporation, and the residue dissolved in ethyl acetate. The organic solution is washed with 0.20 N hydrochloric acid, 5% aqueous sodium bicarbonate, and saturated aqueous sodium chloride. The organic phase is then dried over anhydrous sodium sulfate, filtered, and subjected to evaporation to yield a partial solid in most cases. For a number of compounds, further purification of Compound 6 was deemed unnecessary. Methods which are applicable for the purification of Compound 6 are silica gel chromatography, crystallization in some cases, and gel permeation chromatography using Sephadex TM LH-20 and methanol as a solvent. The latter method is preferred. Typically. NMR spectra indicated the —$CH_2$—Br band at delta 3.45 and a sharp singlet band at delta 0.80–0.95 for one of the methyl group in the pinanediol protecting group or singlet at delta 1.3 for the pinacol group.

The peptide alkyl halide, Compound 6, is then converted to the alkyl azide, Compound 7, by treatment with two equivalents of sodium azide in dimethylformamide at 100° for 3 h. In all cases, this reaction appeared to go smoothly without altering reaction conditions. The NMR spectrum of Compound 7 in $CDCl_3$ typically indicated a delta 0.1–0.2 ppm upfield shift of the —$CH_2$—Br on conversion to the azide. Further purification can be obtained by LH-20 chromatography, but it is not necessary for a many of the peptides.

The boroOrnithine peptides, Compound 8, are prepared routinely by catalytic hydrogenation of the alkyl azides, Compound 7, in the presence of 10% Pd/C and one equivalent of benzene sulfonic acid in alcohol. Hydrogenations are run on a Parr apparatus. Alternately, the hydrogenations can be run at atmospheric pressure and mineral acids can be substituted for benzene sulfonic acid. It should be noted that it is necessary to use peptide protecting groups which are stable to catalytic hydrogenation. Such peptide protecting groups are known to those skilled in the art and are discussed in The Peptides (E. Gross and J. Meienhofer eds.) vol 3, Academic Press, New York, (1981). The preferred protecting groups are the t-butyloxycarbonyl group for amino groups, and t-butyl ethers and esters for hydroxy and carboxylic acid side chains. Other suitable protecting groups include diisopropylmethyloxycarbonyl, t-amyloxycarbonyl, adamantyloxycarbonyl, biphenylisopropyloxycarbonyl and tosyl. It is expected that conversion of the azide to the amine by reduction with other reducing agents can be achieved using reagents such as stannous chloride and trialkyl phosphites as described by Maiti et al., Tetrahedron Lett., 27: 1423–1424 (1986) and Koziara et al., Synthesis, 202–204 (1985). These reagents are expected to be compatible with peptide protecting groups which are labile to catalytic hydrogenation. The boroOrnithine peptides are routinely chromatogramed on Sephadex TM LH-20 and are white amorphous solids after trituration with ether.

BoroArginine peptides, Compound 9, are prepared by allowing the corresponding boroOrnithine peptide, Compound 8, to react with at least a 4-fold excess of cyanamide (50 mg/mL) in absolute ethanol at 100°. Initially the components are allowed to react 2–3 days under a blanket of nitrogen with a water cooled condenser in place. Water cooling is discontinued and the reaction mixture is allowed to concentrate slowly over a period of several days. The completion of the reaction is determined by the progressive increase in the intensity of material staining with Sakaguchi stain for the guanidino group of the boroArginine moiety and the disappearance of material staining positive with ninhydrin stain for the amino group of the boroOrnithine moiety on reverse phase thin layer plates run in methanol:water (85:15). Typically, the boroArginine peptides streaked from the origin of the plate, the boroOrnithine peptides traveled as discrete spots in the middle of the plate, and cyanamide traveled with the solvent front allowing each component to be identified. Specific stains for the guanidino group and the amino group are commonly used in peptide synthesis. Compound 9 was purified by gel permeation chromatography using ephadex TM LH-20 and methanol as a solvent. This chromatographic step readily separates the boroArginine peptides from low molecular weight byproducts and unreacted cyanamide. In most cases, no further purification is needed. However, it is essential that the guanidation reaction of Compound 8 be permitted to run to completion since it is difficult, if not impossible to separate a mixture of Compounds 8 and 9. Final products are obtained as amorphous white solids by trituration with ether and, in most case, are of analytical purity as determined by NMR, mass spectral, and combustion analyses.

It should be noted that guanidation of Compound 8 with cyanamide has been found to be very dependent upon reaction conditions. First, as discussed above, it is important that the reaction be run sufficiently long to result in relatively complete conversion of Compound 8 to Compound 9. Reaction times of up to 7 days and accompanying concentration of reagents by slow evaporation of solvents are often required. In an initial survey of reactions to guanidate Compound 8, Compound 8 as the hydrogen chloride salt, was refluxed with cyanamide in ethanol for several hours. The desired product, Compound 9, was not detectable. Attempts to guanidate Compound 8 using the successful conditions noted above except that tetrahydrofuran was substituted for absolute ethanol failed to yield detectable product. Similarly, when an attempt was made to guanidate Compound 8 using these conditions, except that the benzene sulfonic acid salt of the amino group of the boroOrnithine peptide was neutralized prior to guanidation, Compound 9 was present only at a barely detectable level. The preferred conditions involve reactions with the benzene sulfonic acid salt of Compound 8 (unneutralized). Successful reactions have also been run with the corresponding hydrogen chloride salt.

Usual methods of guanidation of ornithine peptides, to yield the corresponding arginine peptides, used by those skilled in the art of peptide synthesis are the neutralization of the amine of the ornithine peptide and coupling with either S-alkyl or O-alkyl isoureas or guanyl-3,5-dimethylpyrazole nitrate, as described by Barany et al., in The Peptides (E. Gross and J. Meienhofer eds) vol 2, pp. 169–175, Academic Press, New York,(1980). Bannard et al., Can. J. Chem. 36: 1541–1549 (1958) have surveyed different methods of guanidation of amines and found that guanyl-3,5-dimethyl pyrazole is superior to the use of S-methyl isourea and concludes that guanidation with cyanamide is unacceptable although it is described in the early literature. Reactions run with S-methyl isourea hydrogen iodide in ethanol and guanyl-3,5-dimethyl pyrazole under a variety of conditions failed to guanidate the boroOrnithine peptide. The lack of reactivity in this case is probably due to the formation of an internal Lewis acid base complex between the amino group of the ornithine side chain and the boronic acid ester. Synthesis of Compound 9 by the treatment of Compound 6 with guanidine in ethanol was also an unacceptable method of synthesis. Compound 6, approximately 50% pure, was isolated from the reaction of guanidine with 6 in less than 1% yield.

The guanidino group of boroArginine-pinanediol behaves in a fashion similar to the guanidino group of the natural amino acid arginine once it is incorporated into the molecule. For example, the alpha-amino groups can be selectively acylated with an anhydride without effecting the guanidino group of boroArginine. Thus, it is our expectation that Compound 9 can be prepared by the synthesis of H-boroArginine-pinanediol and subsequentially adding the N-protected form of the peptide portion of the molecule using the mixed anhydride procedure and similarily, di-, tri-, etc. peptide analogs containing boroArginine can be extended in length by coupling additional amino acids or peptides.

Additional purification of the protected boroArginine peptides can be achieved by ion exchange chromatography on SP Sephadex ™. The peptides are dissolved in 20% acetic acid and applied to the column in its H+ form. After washing the column with 20% acetic acid, product is eluted by running a gradient from 0–0.3 N hydrochloric acid in 20% acetic acid. The product is eluted as a mixture of pinanediol ester and free peptide boronic acid. A homogenous preparation is obtained by treating the mixture with pinanediol under anhydrous conditions and trituration of the product with ether.

Two procedures have been developed for the removal of the pinanediol protection group to yield the free boronic acid, Compound 10. The first is a modification of the above purification procedure in which a mixture of the free boronic acid and pinanediol ester are co-eluted from the ion exchange column. These compounds are readily separated by chromatography on LH-20. The second procedure is a modification of the method of Kinder et al., J. Med. Chem. 28: 1917–1925 (1985). The boronic acid ester is treated with a 2–3 fold excess of boron trichloride in methylene chloride for 5 min at −78° and the mixture is allowed to stir 15 min in a 0° ice bath. Water is slowly added to hydrolyze excess boron trichloride to boric acid and hydrochloric acid. The reaction is further diluted with 20% acetic acid to yield a final concentration of hydrochloric acid of 0.05 M. The concentration of hydrochloric acid is based on the initial quantity of boron trichloride used in the reaction. The aqueous phase is applied to a SP-Sephadex ™ column and product is eluted as the hydrochloride salt as described above. The free boronic acid peptides were obtained as white amorphous solids.

Compound 10 can be converted to the difluoroborane, Compound 11, using a modification of the procedure of Kinder et al., J. Med. Chem. 28: 1917–1925 (1985). The peptide boronic acid is treated with a 5-fold molar excess of 0.50 N aqueous hydrofluoric acid at room temperature. Excess hydrofluoric acid and water are removed by lyophilization and the resulting solid is triturated with ether to yield desired product as a white amorphous solid.

In the foregoing description, the preparation of the free boronic acid, Compound 10, is from boroArginine-pinanediol ester and the preparation of the difluoroborane acid, Compound 11, is from Compound 10. The procedure for the removal of the ester protecting group should applicable to acyl peptides of boroOrnithine, boroLysine, and boroHomoarginine protected as either pinanediol, pinacol, or other ester protecting group. Similarly, the corresponding free boronic acids can be converted to difluoroboranes.

The preferred side chain protecting groups and N-terminal protecting groups of the peptide portion of molecules are those stable to catalytic hydrogenation and liable to anhydrous hydrogen chloride or trifluoroacetic acid. These criteria are readily met by the t-butyloxycarbonyl amino protecting group and t-butyl ethers and esters for hydroxy and acidic side chains. To remove these groups, the peptides are treated with 4 N hydrogen chloride in dioxane at room temperature. The deprotected peptide is isolated by either evaporating solvent or by precipitation with ether. Particular care should be taken with peptides containing an acidic side chain to remove all hydrogen chloride by evaporation. This insures that the boroArginine peptide is maintained as benzene sulfonic acid salt. Other peptide can be isolated as either a mixed hydrogen chloride-benzene sulfonic acid salt or most can be converted to the hydrogen chloride salt by passage through a anion exchange column in the Cl−ion form.

Isothiouronium derivatives of Compound 6 are prepared by treatment of Compound 6 with thiourea in absolute ethanol to yield Compound 12, analogs of the peptide boroArginine esters, Compound 10. Routinely, the alkyl halides were allowed to stir with a 4–5 fold excess of thiourea for several days at room temperature. The product is separated, when necessary, for unreacted Compound 6 by trituration with ether. Compound 6 is readily soluble in ether for most peptides while the product is insoluble. Final purification, removal of excess thiourea, is achieved by chromatography on Sephadex ™ LH-20 in methanol and trituration with ether to yield final products as hydrogen bromide salts. Side chain and N-terminal protecting groups are removed by treatment with anhydrous hydrogen bromide or other anhydrous acid.

Biological Activity

The biological activity of compounds of the present invention is demonstrated by both in vitro and in vivo data pertaining to inhibition of synthetic substrate hydrolysis by the trypsin-like enzymes, human thrombin and plasma kallikrein, and inhibition of physiological reactions catalyzed by such enzymes such as blood coagulation and inflammation.

In the Examples which follow, the hydrolytic activity of each enzyme is measured in both the presence and absence of inhibitor and the percent enzyme activity determined. It has been found that the most effective inhibitors of both plasma kallikrein and thrombin are slow-binding inhibitors whose effectiveness progressively increases with time until a steady state is reached. A steady state is reached fairly rapidly and nears completion within 5 min. Activity is evaluated between 10–20 min after the components are mixed to insure that reaction components are at equilibrium. The lowest concentration of inhibitor tested is determined by the estimated concentration of enzyme. An inhibitor concentration 5-fold in excess of enzyme concentration is the lowest maintained concentration so that pseudo-first-order reaction conditions are observed. The maintenance of pseudo-first-order reaction conditions and the sensitivity of the respective assays sets the lowest limit level of inhibitor tested at 10 nM for kallikrein inhibitors and 5 nM for thrombin inhibitors.

Usually, reversible inhibitor effectiveness is evaluate by measuring $K_i$'s, the dissociation constants for the enzyme-inhibitor complex. This value, by definition, is the concentration of inhibitor required to inhibit the enzyme 50% in the absence of substrate. But the substrate has a protective effect, therefore higher concentrations of inhibitor are required to achieve 50% inhibition. Nevertheless, a conservative estimate of the $K_i$ can be obtained activity (inhibition) data and the concentration of inhibitor. A level of inhibitor of about 20-fold higher than $K_i$ is required to inhibit a reaction 95% and a level of inhibitor of about 50-fold higher than $K_i$ is required for 98% inhibition.

Plasma kallikrein preferentially hydrolyses and liberates bradykinin. BoroArginine peptides containing Phe adjacent to the boroArginine are the most effective inhibitors of this enzyme. For example, 10 nM H-(D)Phe-Phe-boroArg-$C_{10}H_{16}$ inhibits kallikrein greater than 95%. No significant differences are observed between the effectiveness of the boroArginine pinanediol esters and the corresponding isothiouronium analogs (boroIrg-). In addition, no differences are observed in the effectiveness of the unprotected boronic acid and corresponding difluoroborane.

Results similar to those with kallikrein are obtained for thrombin in assays with synthetic substrates, except that thrombin has a much higher affinity for inhibitors with proline in the site adjacent to the boroArginine. The most effective inhibitor is Ac-(D)Phe-Pro-boroArg-$C_{10}H_{16}$ which inhibits thrombin 99% at a concentration of 5 nM. The most potent inhibitor reported in the literature is N-alpha-(2-naphthylsulfonyl-glycyl)-4-amidinophenylalanine piperidide, which has a $K_i$ of 6 nM. It was reported by B. Kaiser et al., Thromb. Res. 43: 613–620 (1986) and Sturzebecher et al., Thromb. Res. 29: 635–642 (1983). The relationship between inhibitor concentration, $K_i$, and percent inhibition, as previously described, suggests that the $K_i$ of Ac-(D)Phe-Pro-boroArg-$C_{10}H_{16}$ is in the picomolar range. Furthermore, the effectiveness of inhibitors having a (D)Phe-Pro-boroArg- sequence appear relatively insensitive to the presence or absence of, or the nature of an amino terminal protecting group. Such compounds having a Boc and an Ac protecting group and having no protecting group inhibit thrombin similarily, each showing an I.C. 50 of less than 5 nM.

The effectiveness of inhibitors in reactions in which they compete with natural substrates for target enzymes is measured in vitro in blood coagulation assays. Two different assays are used, the APTT (activated partial thromboplastin times) and PT (prothrombin times) assays. These assays mimic the blood clotting process in vivo. Blood coagulation occurs through either of two pathways, each consisting of a cascades of zymogen activation steps. The pathways are termed the intrinsic and the extrinsic pathways (see L. Lorand, Methods in Enzymology 45: 31–37 (1976). The intrinsic pathway is initiated by negatively charged surfaces in which plasma kallikrein, factor XII and factor IX are activated and then factors IX and X and prothrombin are activated in calcium dependent steps. Thrombin, the last protease in the cascade, hydrolyses fibrinogen to fibrin which results in clot formation. In the APTT assay, plasma components are activated by exposure to negatively charged surfaces and then clotting times are measured after calcium is added to the system. In the extrinsic pathway, tissue thromboplastin activates factor VII which then activates factor X leading to the activation of thrombin. These events are measured in the prothrombin times assay.

Peptides of boroArginine and the corresponding isothiouronium analogs effectively inhibit blood clotting in both of these assays. The most effective inhibitors of the present invention for thrombin are the most effective for both assays. On the other hand, inhibitors of kallikrein, while less potent clotting inhibitors, inhibit the APTT assay (kallikrein is involved in the initiation of this assay) more effectively than the PT assay. This is clearly shown in FIG. 1 by the effect of H-(D)Phe-Pro-boroArg-$C_{10}H_{16}$ (thrombin inhibitor) on the relative clotting times of plasma. It demonstrates the selectivity which can be achieved by varying a single amino acid in the tripeptide inhibitor in a rather complex biological system. The effective levels of thrombin inhibitors are in the same molar range as heparin. Usually, 0.2–0.4 units of heparin per mL of plasma increases clotting times 2–2.5 fold. If one assumes an average molecular weight of 15,000 for heparin and specific activity of 150 units/mg, its molar concentration is 86–170 nM. The concentration of the boroArginine peptides required to increase clotting times in the APTT assay are in the range of 170–230 nM. It should be noted that heparin is a cofactor for the high molecular weight protease inhibitor, anti-thrombin III.

The stability of the boroArginine peptides in human plasma is shown by incubating them with plasma at a concentration effective to delay the clotting process. Samples of the inhibitors are removed at increasing time intervals and their ability to delay clotting is measured at each interval. No change in the clotting time indicates no change in the inhibitory activity of the inhibitors during incubation in plasma. No significant change in inhibitor activity was observed except for H-(D)Phe-Pro-boroArg-$C_{10}H_{16}$, which lost activity after 24 h. The inhibitors of this invention are also stable for 24 h in phosphate buffer at pH 7.5 except for H-(D)Phe-Pro-boroArg-$C_{10}H_{16}$, which lost inhibitory activity within one hour. The greater instability of this inhibitor in buffer suggests that phosphate buffer plays a role in destabilizing the compound.

The in vivo data supplied clearly indicates the efficacy of the subject compounds as inhibititors of blood coagulation in mammalian systems.

Compounds of the present invention are also effective anti-inflammatory agents as shown by the inhibition of rat ear edema when the compounds are applied topically along with with an irritant. The molecular basis for this pharmacological activity is unknown, since multiple events occur during inflammation. However, proteases which increase vascular permeability, such as plasma kallikrein which liberates kinins and enzymes of the complement system which liberate the anaphylatoxin peptides, are thought to be implicated in the inflammatory process.

Finally, peptides of boroLysine were shown to effectively inhibit plasmin, an enzyme which plays a key role in hemostasis.

Utility

N-Acyl and N-peptide alpha-aminoboronic acids which are analogs of ornithine, arginine, lysine and homoarginine of the present invention represent a novel class of potent, reversible inhibitors of trypsin-like enzymes. Trypsin-like enzymes are a group of proteases which hydrolyze peptide bonds at basic residues liberating either a C-terminal arginyl or lysyl residue. Among these enzymes are the proteases of the blood coagulation system (factors, XIIa, XIa, IXa, VIIa, Xa, and thrombin), the fibrinolytic system (plasminogen activators and plasmin), the complement system (C1s, C1r, C3 convertase, factor D, etc.), pancreatic trypsin (which as a digestive function), and acrosin, (which is a protease associated with sperm and required for fertilization).

The ability of the compounds of this invention to inhibit trypsin-like proteases has been determined by inhibiting two different trypsin-like enzymes, human thrombin and plasma kallikrein. Compounds of the present invention are much more potent inhibitors of both of these enzymes than other known reversible inhibitors. For example, the most effective inhibitor of thrombin reported to date is N-alpha-(2-naphthyl-sulfonyl-glycyl)-4-amidinophenylalanine piperidine which a $K_i$ of 6 nM. Compounds of the present invention almost completely inhibit thrombin at a concentration of 5 nM indicating a $K_i$ of <1 nM, and thus provide excellant candidates for the control of thrombin mediated processes such as blood coagulation. The most effective boroArginine peptide inhibits blood clotting as demonstrated by the increase in the APT times and PT times. Its level of effectiveness is similar to that of heparin on a molecular basis. In addition, the compounds are stable in human plasma. The compounds can be used as anticoagulants in the preparation of plasma for protein isolation as well as for clinical testing.

An additional example is the protease, plasmin, which has a pivotal role in the lysis of blood clots. Peptides containing borolysine were prepared and tested and found to be active inhibitors of plasmin.

Compounds of the present invention are effective in controlling proteolysis in vivo and should be pharmaceutically effective in the treatment of diseases in mammals arising from uncontrolled protease activity. Notable among these are conditions associated with thrombosis and consumptive coagulopathy. Coronary thrombosis plays an important contributing role in myocardial infarction. Consumptive coagulopathy, a condition marked by decreases in blood coagulation factors and plasma protease inhibitor, is observed in patients with acute pancreatitis and disseminated intravascular coagulation (DIC). It is expected that compounds of the present invention can be used in place of heparin with the advantage that heparin's plasma cofactor, antithrombin III, is not consumed in the reaction. Also, thrombocytopenia, a side effect of heparin treatment, should not be observed. Furthermore, compounds of the present invention are expected to be valuable in the treatment of diseases in which there is a deficiency of natural inhibitors of trypsin-like enzymes such as heritary edema. This disorder arises from a deficiency of C1 inhibitor, the major inhibitor of plasma kallikrein.

Finally, compounds of the present invention have demonstrated effective anti-inflammatories activity in vivo.

Synthesis Examples

The examples which follow illustrate particular embodiments of the invention. All melting points reported are uncorrected. All parts are by weight and all temperatures are reported in degrees Celsius. Proton nuclear magnetic resonance (NMR or 1H NMR) reports chemical shifts in delta units, parts per million downfield from the internal tetramethylsilane standard. Various abbreviations employed throughout include: TFA=trifluoracetic acid; DMF=N,N-dimethylformamide; MS=mass spectrometry; TLC=thin layer chromatography; RP-TLC=reverse phase thin layer chromatography. The ester protecting groups for the boronic acids are abbreviated: $-C_4H_{12}$=the pinacol group and $-C_{10}H_{16}$=the pinanediol group. "Irg" is the abbreviation for the isothiouronium analog of arginine (Arg) and the prefix "homo" indicates structures in which the side chain contains an additional methylene group. All amino acid residues are in the "L" configuration unless specified.

TLC and RP-TLC were conducted on E. Merk Silica Gel 60 Plates (Catalog #5534, E. M. Sciences, Gibbstown, NJ) and Whatman KC18F Reverse Phase Plates (Catalog #4803-600, Whatman Co., Clifton, NJ), respecively. Neutral compounds were visualized under UV light and after exposure to iodine vapors. Compounds with free amino groups were stained with ninhydrin and compounds with guanidino groups were stained with the Sakaguchi stain. The Sakaguchi stain exhibits a considerable specificity for the monosubstituted guanidines such as those present in the boroArginine peptides (see Chemistry of the Amino Acids, 3: (1984) Greenstein and Winitz, eds., Robert E. Krieger Publishing Co., Malabar, FL).

EXAMPLE 1a

1-Amino-4-bromo-butyl boronate pinanediol.hydrogen chloride, $NH_2-CH[(CH_2)_3Br]BO_2-C_{10}H_{16}.HCl$ 4-Bromo-1-chlorobutyl boronate pinanediol was prepared by the method in Matteson et al., Organometallics 3: 1284-1288 (1984), except conditions were modified for large scale preparations. In a typical experiment, allyl bromide (173 mL, 2.00 moles) was hydroborated with catechol borane (240 mL, 2.00 moles) by the addition of the borane to allyl bromide and then heating the reaction for 4 h at 100° under a nitrogen atmosphere. The product, 3-bromopropyl boronate catechol (bp 95°-102°, 0.25 mm) was isolated in a yield of 49% by distillation. The catechol ester (124 g, 0.52 moles) was transesterified with (+)alpha-pinanediol (88 g, 0.52 moles) by mixing the component in 50 mL of tetrahydrofuran (THF) and allowing them to stir for 0.5 h at 0° and 0.5 h at room temperature. Solvent was removed by evaporation and 250 mL of hexane was added. Catechol was removed as a crystalline solid. Quantitative removal was achieved by successive dilution to 500 mL and to 1000 mL with hexane and removing crystals at each dilution. Product (147 g) was obtained as an oil by evaporating solvent.

Analysis for $C_{13}H_{22}O_2BrB$: Calculated: C=51.85%, H=7.38%, and Br=26.54. Found: C=52.85%, H=7.30%, and Br=26.58%.

4-Bromo-1-chlorobutyl boronate pinanediol was prepared by homologation of the corresponding propyl boronate. Methylene chloride (34.8 mL, 0.540 moles) was dissolved in 500 mL of THF, 1.54 N n-butyllithium in hexane (350 mL, 0.540 moles) and was slowly added at −100°. 3-Bromopropyl boronate pinanediol (148 g, 0.490 moles) was dissolved in 500 mL of THF, cooled to the freezing point of the solution, and added to the reaction mixture. Zinc chloride (33.5 g, 0.246 moles) was dissolved in 250 mL of THF, cooled to 0°, and added to the reaction mixture in several portions. The reaction mixture, while stirring, was allowed to warm slowly overnight to room temperature. Solvent was evaporated and the residue was dissolved in hexane and washed with water. After drying over anhydrous magnesium sulfate and filtering, solvent was removed to yield the desired product (140 g).

1-Amino-4-bromobutyl boronate pinanediol was prepared first by dissolving hexamethyldisilizane (28.0 g, 80.0 mmoles) in 30 mL of THF, cooling the solution to −78°, and adding 1.62 N n-butyllithium in hexane (49.4 mL, 80.0 mmoles). The solution was allowed to slowly warm to room temperature and was then recooled to −78° and 4-bromo-1-chlorobutyl boronate pinanediol (28.0 g, 80.0 mmoles) in 20 mL of THF was added. The mixture was allowed to slowly warm to room temperature and to stir overnight. Solvent was removed by evaporation and dry hexane (400 mL) was added to yield a precipitate which was removed by filtration under an nitrogen atmosphere. The filtrate was cooled to −78° and 4 N hydrogen chloride in dioxane (60 mL, 240 mmoles) was added. The reaction was allowed to warm slowly to room temperature, at which temperature it was stirred for 2 h. The resulting product (20 g) was isolated as a solid by filtration. After drying in vacuo, the crude product was dissolved in chloroform and insoluble material was removed by filtration. The filtrate was evaporated and the residue dissolved in ethyl acetate. The product crystallized from ethyl acetate to yield 15.1 g (mp 142°-144.5°). $[\alpha]_D^{25} = +16.7 \pm 0.80$, C=1.0 in absolute ethanol.

Analysis for $C_{14}H_{26}NO_2BrClB$: Calculated: C=45.87%, H=7.16%, N=3.82%, and B=2.95%. Found: C=45.76%, H=7.21%, N=3.79%, and B=3.04%.

EXAMPLE 1b (D,L)1-Amino-4-bromobutyl boronate pinacol.HCl
(D,L)$NH_2$-$CH[(CH_2)_3Br]BO_2$—$C_6H_{12}$.HCl 4-bromo-1-chlorobutyl boronate pinacol was prepared by the method described for the corresponding pinanediol (Example 1a) except pinacol was substituted for pinanediol and 3-bromopropyl boronate pinacol (bp 60°-64°, 0.35 mm) and 4-bromo-1-chlorobutyl boronate pinacol (bp 110°-112°, 0.20 mm) were distilled.

Analysis for $C_{10}H_{19}O_2BrClB$: Calculated: C=40.38% and H=6.45%. Found: C=40.70% and H=6.37%.

1-Amino-4-bromobutyl boronate pinacol.hydrogen chloride was also prepared by the procedure in Example 1a. The final product was crystallized for ethyl acetate:hexane in yield of 52%.

Analysis for $C_{10}H_{22}NO_2BrClB$: Calculated: C=38.19%, H=7.05%, N=4.45%, Cl=11.27% and Br=25.41%. Found: C=38.28%, H=7.39%, N=4.25%, Cl=11.68% and Br=26.00%.

EXAMPLE 1c

1-Amino4-chlorobutyl boronate pinacol.hydrogen chloride (D,L)$NH_2$-$CH[(CH_2)_3Cl]BO_2$—$C_6H_{12}$.HCl 3-Chloropropyl boronate catechol (bp 80-85o, 0.30 mm) and 3-chloropropyl boronate pinacol(bp 63°, 0.20 mm) were prepared by the method in Example 1a except allyl chloride was substituted for allyl bromide and pinacol was substituted for pinanediol.

Analysis for $C_9H_{18}O_2ClB$: Calculated: C=52.85, H=8.89%, and Cl=17.33%. Found: C=53.41%, H=8.15%, and Cl=16.81%.

Homologation was also conducted by the procedure in Example 1a and the product was isolated by distillation (bp 95°, 0.25 mm) in a yield of 65%.

Analysis for $C_{10}H_{19}O_2Cl_2B$: Calculated: C=47.47%, H=7.58%, and Cl=28.02%. Found: C=47.17%, H=7.45%, and Cl=27.75.

1-Amino-4-chlorobutyl boronate pinacol.HCl was prepared by a procedure identical to Example 1a. The product crystallized from ethyl acetate to yield 8.8 g (mp 132°-135.5°) and 2.2 g (mp 145°-147°). The product melting 145°-147° was used for analyses.

Analysis for $C_{10}H_{22}NO_2Cl_2B$: Calculated: C=44,47%, H=8.23%, and N=5.19%, and B=4.00%. Found: C=44.01%, H=8.23%, N=4.77%, and B=3.80%.

EXAMPLE 1d (D,L)1-Amino-5-bromopentyl boronate-pinacol.HCl
(D,L)$NH_2$-$CH[(CH_2)_4Br]BO_2C_6H_{12}$.HCl 4-bromobutyl boronate pinacol was prepared by the method described for 3-bromopropyl boronate pinanediol (Example 1a) except 4-bromo-1-butene was substituted for allyl bromide and pinacol was substituted for pinanediol. The product was isolated as an oil (bp 77°, 0.3 mm). Homologation yielded 5-bromo-1-chloropentyl boronate pinacol.

MS(CI) for $C_{11}H_{21}O_2BrClB$: Calculated—H: 310.47. Found: 310.

The final product, 1-amino-5-bromopentyl boronate pinacol.HCl, was prepared by the procedure in Example 1a in a yield of 35%.

Analysis for $C_{11}H_{24}NO_2BrBCl$: Calculated: C=40.22%, H=7.36%, N=4.26%, Cl=10.79%, Br=24.32%, and B=3.29%. Found: C=39.23%, H=7.18%, N=4.04%, Cl=15.21% and Br=25.66%, and B=3.75%

EXAMPLE 2

D)Phe-Pro-NH-$CH[(CH_2)_3Br]BO_2$-$C_{10}H_{16}$

Boc-(D)Phe-Pro-OH was produced by first preparing the dipeptide benzyl ester and then removing the ester by catalytic hydrogenation. Boc-(D)Phe-OH (10.0 g, 37.7 mmoles) was dissolved in 50 mL of THF and N-methylmorpholine (4.14 mL, 37.7 mmoles) was added. The solution was cooled to −20° and isobutyl chloroformate (4.90 mL, 37.7 mmoles) was added. After 5 min, H-Pro-OBzl.HCl (9.11 g, 37.7 mmoles), dissolved in chloroform and cooled to −20°, was added. Triethylamine (5.25 mL, 37.7 mmoles) was added and the mixture was stirred for 1 h at −20° and 2 h at room temperature. The reaction mixture was filtered and the filtrate evaporated. The residue was dissolved in ethyl acetate and was washed with 0.2 N hydrochloric acid, 5% aqueous sodium bicarbonate, and saturated aqueous sodium chloride. The organic phase was dried over anhydrous sodium sulfate, filtered, and evaporated to yield 15.2 g of Boc-(D)Phe-Pro-OBzl as an oil. The benzyl ester (15.2 g) was dissolved in 100 mL of methanol and it was hydrogenated at an initial pressure of 40 psi on a Parr apparatus in the presence of 0.5 g of 10% Pd/C. The reaction solution was filtered through Celite ™ and evaporated to yield a solid. This solid material was isolated and was washed with ethyl acetate and then by ether to yield 10.0 g of the desired product (mp 176.5°-177°).

Analysis for $C_{19}H_{26}N_2O_5$: Calculated: C=62.95%, H=7.24%, and N=7.73%. Found: C=62.91%, H=7.15%, and N=7.53%.

Boc-(D)Phe-Pro-NH-$CH[(CH_2)_3Br]BO_2$-$C_{10}H_{16}$ was prepared by coupling the dipeptide to the corresponding amine using the mixed anhydride procedure. The mixed anhydride of Boc-(D)Phe-Pro-OH was prepared by dissolving this acid (4.94 g, 13.6 mmoles) in 30 mL of THF and adding N-methylmorpholine (1.50 mL, 13.6 mmoles). The solution was cooled to −20° and isobutyl chloroformate (1.77 mL, 13.6 mmoles) was added. After stirring for 5 min at −20°, the mixture was added to the amine as in Example 1a, $NH_2$—$CH[(CH_2)_3Br]BO_2$-$C_{10}H_{16}$.HCl, (5.0 g, 13.6 mmoles) dissolved in 10 mL of cold chloroform. Cold THF (10 mL) and triethylamine (1.90 mL, 13.6 mmoles) were added and the mixture was stirred for 1 h at −20° and approximately 2 h at room temperature. The mixture was filtered and the liquid in the filtrate was evaporated. The residue was dissolved in ethyl acetate and washed with 0.2 N hydrochloric acid, 5% aqueous sodium bicarbonate, and saturated aqueous sodium chloride. The organic phase was dried over anhydrous sodium sulfate, filtered, and the solvent evaporated to yield 9.0 g of an oil. This material was dissolved in methanol and chromatogramed on a 2.5×50 cm column of LH-20. Fractions containing the desired product were pooled and evaporated to yield 5.8 g of a solid. TLC with methanol:chloroform (1:9) indicated a single spot, Rf 0.70.

MS(FAB) for $C_{33}H_{49}N_3O_6BBr$: Calculated +H: 674.30 Found: 674.30

EXAMPLE 3

D)Phe-Pro-NH-CH[$(CH_2)_3N_3$]BO$_2$-C$_{10}$H$_{16}$

Boc-(D)Ph--Pro-NH-CH[$(CH_2)_3Br$]BO$_2$-C$_{10}$H$_{16}$, the product of Example 2, (4.4 g, 6.54 mmoles) was dissolved in 7 mL of DMF and sodium azide (0.919 g, 14.1 mmoles) was added. The mixture was heated at 100° for 3 h. Ethyl acetate (100 mL) was added to the reaction mixture and it was washed with water and with saturated aqueous sodium chloride. The organic phase was dried over anhydrous sodium sulfate, filtered, and subjected to evaporation. A yield of 4.1 g of a solid resulted. This material was chromatographed on a 2.5×50 cm column of LH-20 in methanol. Fractions containing the desired product were pooled, liquid was evaporated to yield 2.3 g of the azide. TLC in methanol:chloroform (1:9) indicated a single spot, Rf 0.76.

Analysis for $C_{33}H_{48}N_6O_6B$: Calculated: C=62.35%, H=7.63%, N=13.33%, and B=1.70%. Found: C=63.63%, H=8.02%, N=11.58%, and B=1.80%. MS(FAB) for $C_{33}H_{48}N_6O_6B$ Calculated +H: 637.39. Found: 637.49.

EXAMPLE 4

Boc-(D)Phe-Pro-NH-CH[$(CH_2)_3NH_2$]BO$_2$-C$_{10}$H$_{16}$.benzene sulfonic acid The azide of Example 3, (8.80 g, 13.8 mmoles) was dissolved in 150 mL of methanol and was hydrogenated on a Parr apparatus at 40 psi in the presence of 0.50 g of 10% Pd/C and benzene sulfonic acid (2.19 g, 13.8 mmoles). After 1 h, catalyst was removed and the solution was evaporated to yield a solid which was triturated with hexane to yield 9.9 g of the desired product. RP-TLC in methanol:water (85:15) indicated a UV spot, RF 0.91, and a ninhydrin positive spot, RF 0.52.

EXAMPLE 5

Boc-(D)Phe-Pro-NH-CH[$(CH_2)_3$—NH—C(NH)NH$_2$]BO$_2$-C$_{10}$H$_{16}$. benzene sulfonic acid Boc-(D)Phe-Pro-boroArg-C$_{10}$H$_{16}$.benzene sulfonic acid Boc-(D)Phe-Pro-boroOrn-C$_{10}$H$_{16}$.benzene sulfonic acid, Example 4, (4.6 g, 6.11 mmoles) was refluxed at 00° in 20 mL of absolute ethanol containing cyanamide (50 mg/mL). The progress of the reaction was monitored by RP-TLC in methanol:water (85:15) in which the disappearance of the ninhydrin spot for the amine starting material (Rf 0.54) and the appearance of the Sakaguchi streak of the product (Rf 0–0.13) was observed. Product could be detected after refluxing 18 h and its level progressively increased with time. After 7 days, amine could not be detected and the reaction solution was concentrated to an approximate 50% solution through passive evaporation. The reaction solution was filtered, concentrated, and chromatographed on a 2.5×100 cm column of LH-20 in methanol. Fractions containing the desired product were pooled and subjected to evaporation to yield 3.7 g of the desired product. A portion (2.3 g) was crystallized for ethyl acetate:-hexane to yield 0.89 g and the residue (1.2 g) was obtained as a solid by triturating with ether. In separate experiments.

MS(FAB) for $C_{34}H_{53}N_6O_6SB$: Calculated +H: 653.42 Found: 653.38

Analysis for $C_{40}H_{59}N_6O_9SB.H_{20}$ Calculated: C=57.95%, H=7.43%, N=10.14%, and B=1.30%. Found: C=57.20%, H=7.14%, N=10.94%, and B=1.01%.

EXAMPLE 6

H-(D)Phe-Pro-boroArg-C$_{10}$H$_{16}$.2HCl

Boc-(D)Phe-Pro-boroArg-C$_{10}$H$_{16}$.benzene acid, the product of Example 5, (1.17 g, 1.54 mmoles) was reacted with 5 mL of 4 N hydrogen chloride in dioxane for 15 min at room temperature. The product was precipitated by the addition of ether, isolated, and washed with ether and dried in vacuo. It was then dissolved in 10 mL of water and applied to a 5 mL anion exchange column of BIO-RAD AGI X8 TM (Cl⁻ form, BIO-RAD Co., Richmond, CA) and the column was washed with water (approximately 30 mL). The effluent was evaporated in vacuo and the residue was triturated with ether to yield the desired product(0.80 g).

MS(FAB) for $C_{29}H_{45}N_6O_4B$: Calculated +H: 553.37. Found: 553.40 and 538.40 (unidentified). Analysis of H-(D)Phe-Pro-boroArg-C$_{10}$H$_{16}$.1BSA.TFA: Found: 553.4

EXAMPLE 7-8

Ac-(D)Phe-Pro-boroArg-C$_{10}$H$_{16}$.HCl (Example 7)

Ac-(D)Phe-Pro-boroArg-OH.HCl (Example 8)

Boc-(D)Phe-Pro-boroArg-C$_{10}$H$_{16}$.benzene sulfonic acid, the product of Example 5, (0.86 g, 1.13 mmoles) was reacted with anhydrous TFA (approximately 5 mL) for 15 min at room temperature. Excess TFA was removed by evaporation and the residue was triturated with ether to yield 0.76 g. This product (0.70 g, 0.91 mmole) was dissolved in a mixture consisting of 2 mL of dioxane and 1 mL of water. Acetic anhydride (0.47 mL, 5.0 mmoles) and sodium bicarbonate (0.42 g, 5.0 mmoles) were added. The mixture was stirred for 20 min at room temperature. Ethyl acetate (50 mL) and water (5 mL) were added. The phases were separated and the organic phase was dried over anhydrous sodium sulfate, filtered, and solvent removed by evaporation to yield 0.56 g of a partial solid.

· The sample was dissolved in 4 mL of glacial acetic acid and diluted with 16 mL of water. It was immediately applied to a column containing 15 mL of SP-Sephedex TM (H⁺ form) and equilibrated with 20% acetic acid. The column was washed with 300 mL of 20% acetic acid and then a linear gradient from 100 mL of 20% acetic acid to 100 mL of 20% acetic acid adjusted to 0.30 N hydrochloric acid was run. Fractions collected from 0.08 to 0.17 N hydrochloric acid contained the N-acetyl peptide (0.29 g) as a mixture of the free boronic acid and pinanediol ester.

The pinanediol ester and the free boronic acid were separated by chromatography on a 2.5×100 cm column of LH-20 in methanol. The fraction size was 8.2 mL. The pinanediol ester (102 mg) eluted in fraction 41-43 while free boronic acid (131 mg) slowly eluted in fractions 45-129.

MS(FAB) (Example 7): Ac-(D)Phe-Pro-boroArg-$C_{10}H_{16}$) for $C_{31}H_{47}N_6O_5B$: Calculated+H: 595.33. Found: 595.33. MS (FAB) (Example 8): Ac-(D)Phe-Pro-boroArg-OH HCl) for $C_{21}H_{33}N_6O_5$: Calculated+H: 449.60. Found 579.24-581.24.

The latter result could not be interpreted. However, NMR was consistent with the structure of the free boronic acid since definitive bands for pinanediol group such as the methyl groups singlets observed at delta 0.85(3H), 1.30(3H), and 1.36(3H) were absent. As added proof of structure, a sample of the free boronic was re-esterified to give the product in Example 7. An analytical sample (20 mg) was treated with a 2-fold excess of pinanediol (14 mg) in 3 mL of methanol for 5 min. Solvent was evaporated and excess pinanediol was removed by trituration of the sample with ether to yield the product (26 mg).

MS(FAB) (Found: 595.38) and NMR were consistent with that expected for the esterified product and were almost identical to the pinanediol product of Example 7.

EXAMPLE 9

Ac-Phe-boroArg-$C_{10}H_{16}$.HCl

Ac-Phe-NH-CH[$(CH_2)_3$Br]$BO_2$—$C_{10}H_{16}$ was prepared by the procedure described in Example 2. The mixed anhydride of Ac-Phe-OH (0.565 g, 2.73 mmoles) was prepared in 10 mL of THF and coupled to $NH_2$—CH[$(CH_2)_3$Br]$BO_2$-$C_{10}H_{16}$.HCl (the product of Example 1a, 1.00 g, 2.73 mmoles) dissolved in 10 ml of cold THF to yield 1.47 g of a white foam. This material was stirred with hexane overnight to yield a solid, 1.01 g (mp 106.5°-109°).

Analysis for $C_{25}H_{36}N_2O_4BrB$: Calculated: C=57.81, H=7.00%, N=5.40%, Br=15.40%, B=2.08%. Found: C=58.33%, H=7.33%, N=4.76%, Br=14.18%, B=1.80%. MS(FAB) for $C_{25}H_{36}N_2O_4BrB$: Calculated+H: 519.20. Found: 519.23.

Ac-Phe-NH-CH[$(CH_2)_3N_3$]$BO_2$-$C_{10}H_{16}$ was prepared by treating Ac-Phe-NH-CH[$(CH_2)_3$Br]$BO_2$-$C_{10}H_{16}$ (3.22 g, 6.20 mmoles) with sodium azide by the procedure described in Example 3. Product from the reaction (3.03 g) was chromatographed on LH-20. Fractions containing the desired product were pooled and evaporated. The residue was triturated with hexane to yield 2.21 g of the azide.

Ac-Phe-boroOrn-$C_{10}H_{16}$.benzene sulfonic acid was prepared from Ac-Phe-NH-CH[$(CH_2)_3N_3$]$BO_2$-$C_{10}H_{16}$ (2.21 g, 4.59 mmoles) by the procedure in Example 4 except hydrogenation was performed at atmospheric pressure. After filtration, and the evaporation of solvent, the desired product (2.22 g) was obtained by triturating with ether.

Ac-Phe-boroArg-$C_{10}H_{16}$.benzene sulfonic acid was prepared by treating Ac-Phe-boroOrn-$C_{10}H_{16}$.benzene sulfonic acid (2.0 g, 3.26 mmoles) with a 10 mL solution of cyanamide (100 mg/mL) in ethanol. The guanidation procedure in Example 5 was used except the reaction time was 3 days and the reaction mixture contained a mixture of starting material and product. This required an additional purification step which most probably could have been eliminated by a longer reaction time. The solution was concentrated and chromatogramed on 2.5×100 cm column of LH-20 in methanol. The fractions containing the desired product, detected by Sakaguchi stain, were pooled and subjected to evaporation to yield 1.4 g. The resulting material (1.2 g) was dissolved in 6 mL of acetic acid and diluted with 30 mL of water to yield a milky solution. It was applied to a 30 mL column of SP-Sephedex ™ C-25 (H+form) equilibrated in 20% aqueous acetic acid. The column was washed with 240 mL of 20% acetic acid and then a linear gradient form 250 mL of 20% acetic acid to 250 mL of 20% acetic acid containing 0.30 N hydrochloric acid was run. Fractions eluted from the column from 0.12 N to 0.16 N hydrochloric acid were pooled to yield 0.42 g of the desired peptide as a mixture of the free boronic acid and pinanediol ester. The mixture was dissolved in methanol (10 ml) and 80 mg of pinanediol was added to esterify the free boronic acid. After stirring for 30 min, solvent was evaporated and the residue was triturated with ether to yield 0.28 g of the desired product.

Analysis for $C_{26}H_{40}N_5B_4HCl.2H_2O$: Calculated: C=54.78%, H=8.15%, N=12.30%, and B=1.90. Found: C=55.34, H=7.83, N=11.66, and B=1.99. MS(FAB) for $C_{26}H_{40}N_5O_4B$: Calculated+H: 498.32. Found: 498.31.

EXAMPLE 10

Ac-(D,L)Phe-(D,L)boroArg-$C_6H_{12}$

The intermediate, Ac-(D,L)Phe-(D,L)-NH-CH[$(CH_2)_3$Br]$BO_2$-$C_6H_{12}$, was prepared by a modification of the procedures of Examples 1b and 2. The acid chloride of Ac-Phe-OH was prepared by reacting Ac-Phe-OH (30 g, 0.145 moles) with phosphorous pentachloride (30 g, 0.144 moles) in 175 mL of THF at −10°. The reaction was stirred at 0° for approximately 1 h, then diluted to a volume of 350 mL with cold ether. The product was isolated as a solid, washed with cold ether, and dried in vacuo to yield 21 g. The activated Ac-Phe derivative (14.8 g, 65.6 mmoles) was dissolved in 40 mL of THF and added to the product of the reaction of 4-bromo-1-chlorobutyl boronate pinacol and hexamethyldisilizane (prepared on a 20 mmole scale) at −78°. The reaction mixture was allowed to warm to room temperature then stirred overnight. The solvent was removed by evaporation. The residue was dissolved in ethyl acetate and washed successively with water, 5% sodium bicarbonate solution and a solution of saturated aqueous sodium chloride. The organic phase of the resulting mixture was dried over anhydrous sodium sulfate and concentrated to yield the desired product as a crystalline solid (1.37 g, mp 146.5°-148°). In a separate experiment, the following analysis was obtained.

Analysis for $C_{21}H_{32}N_2O_4BrB$: Calculated: C=53.98%, H=6.92%, N=6.00%, Br=17.10%, and B=2 31%. Found: C=54.54%, H=6.78%, N=5.89%, Br=16.46%, and B=3.40%.

The alkyl bromide was converted to the corresponding azide by the procedure in Example 3. The product crystallized from ethyl acetate (mp 143°-144°).

Analysis for $C_{21}H_{32}N_2O_4B$: Calculated: C=58.74%, H=7.53%, N=16.31%, and B=2.53%. Found: C=58.85%, H=7.48%, N=16.53%, and B=2.93%.

The azide was converted to Ac-(D,L)Phe-(D,L)boroOrn-$C_6H_{12}$.benzene sulfonic acid by the procedure in Example 4 except hydrogenation was conducted at atmospheric pressure.

Ac-(D,L)Phe-(D,L)boroOrn-C6H12.benzene sulfonic acid (0.243 g, 0.433 mmoles) was reacted with cyanamide (0.020 g, 0.476 mmoles) at 100° in 2 mL of absolute ethanol overnight. The solution was concentrated and triturated with ether to yield 0.21 g of a white solid. RP-TLC of the material indicated the characteristic streak staining positive with the Sakaguchi stain for the boroArginine peptides, Rf 0–0.55, and a discrete spot, Rf 0.68, corresponding to unreacted starting material. The product (81 mg) was retreated with 2 mL of cyanamide (10 mg/mL) overnight by the above procedure to yield 71 mg after trituration with ether.

MS(FAB) for $C_{22}H_{37}N_5O_4B$: Calculated + H: 446.30. Found: 446.23 and 404.19 (corresponding to the unreacted boroOrn peptide).

Note that the method of Example 5 is a superior method for preparing the boroArginine peptides and differs in that a larger excess of cyanamide and longer reaction times are used.

EXAMPLE 11

Boc-(D)Phe-Phe-boroArg-$C_{10}H_{16}$.benzene sulfonic acid

Boc-(D)Phe-Phe-OH was prepared by the method described for Boc-(D)Phe-Pro-OH in Example 2. Following hydrogenation of the benzyl ester, material crystallized from chloroform:hexane yielding the desired peptide (mp 133°–133.5°).

Analysis for $C_{23}H_{28}N_2O_5$: Calculated: C=66.96%, H=6.86%, and N=6.79%. Found: C=66.75%, H=6.79%, and N=6.56%.

Boc-(D)Phe-Phe-NH-CH[$(CH_2)_3$Br]$BO_2$—$C_{10}H_{16}$ was prepared by coupling Boc-(D)Phe-Phe-OH (6.00 g, 14.5 mmoles to $NH_2$—CH[$(CH_2)_3$Br]$BO_2$—$C_{10}H_{16}$.HCl (Example 1a, 5.33 g, 14.5 mmoles) using the procedure described in Example 2 except that the LH-20 chromatography step was eliminated. The product crystallized from ethyl acetate to yield 2.47 g (mp 132°–134°) in the first crop and 5.05 g (mp 133°–135°) in a second crop. RP-TLC in methanol:water (85:15) indicated a single spot, RF 0.29.

Analysis for $C_{37}H_{51}N_3O_6BrB$: Calculated: C=61.32%, H=7.11%, N=5.80%, Br=11.03%. Found: C=61.21%, H=7.02%, N=5.59%, Br=10.22%.

Boc-(D)Phe-Phe-NH-CH[$(CH_2)_3N_3$]$BO_2$-$C_{10}H_{16}$ was prepared by treating the corresponding alkyl bromide (7.15 g, 9.87 mmoles) with sodium azide using the procedure in Example 3, except the LH-20 chromatography step was not needed for purification. The product emerged from an ethyl acetate:hexane solution as a gel and was isolated and washed with hexane to yield 3.0 g in the first crop and 2.9 g in a second crop.

Boc-(D)Phe-Phe-boroOrn-$C_{10}H_{16}$.benzene sulfonic acid was prepared from the azide (5.37 g, 7.82 mmoles) by the procedure in Example 4 to yield 5.33 g. RP-TLC methanol:water (85:15) indicated an intense ninhydrin positive spot, Rf 0.42, and a weak ultraviolet (UV) light spot, 0.92. (The UV spot at Rf 0.92 is typical of amines or guanidino compounds which are benzene sulfonic acid salts.)

MS(FAB) for $C_{37}H_{53}N_4O_6B$: Calculated + H: 661.76. Found: 661.14.

Boc-(D)Phe-Phe-boroArg-$C_{10}H_{16}$ was obtained by the procedure in Example 5. The boroOrnithine peptide (4.83 g, 5.90 mmoles) was treated with cyanamide (50 mg/mL) in 20 mL of absolute ethanol for 7 days. A portion of the reaction mixture corresponding to 1.0 g of starting material was removed and heated separately in the absence of a reflux condenser overnight to obtain complete conversion of the amine to the guanidino compound. Following chromatography on LH-20 and trituration of the product with ether, 0.52 g of the desired product were obtained.

Analysis for $C_{44}H_{16}N_6O_9SB$: Calculated: C=61.38%, H=7.16%, N=9.76%, B=1.25%. MS(FAB) for $C_{38}H_{55}N_6O_6B$ Calculated + H: 703.43. Found: 703.49.

EXAMPLE 12

H-(D)Phe-Phe-boroArg-$C_{10}H_{16}$.2HCl

Boc(D)Phe-Phe-boroArg-$C_{10}H_{16}$.benzene sulfonic acid (Example 11, 0.59 g, 1.25 mmoles) was deblocked by the procedure in Example 6 except that the sample was applied to the ion exchange column in 20% ethanol and the column was eluted with 20% ethanol. The product (0.424 g) was obtained as a white solid.

MS(FAB) for $C_{33}H_{47}N_6O_4B$: Calculated + H: 603.38. Found: 603.41.

EXAMPLE 13

Ac-Ala-Lys(Boc)-boroArg-$C_{10}H_{16}$.benzene sulfonic acid

Ac-Ala-Lys(Boc)-OH was prepared by coupling the N-hydroxysucoinimide ester of Ac-Ala-OH, prepared by the method of Anderson et al., J. Am. Chem. Soc. 86: 1839, (1964), to H-Lys(Boc)-OH. The N-hydroxysuccinimide of Ac-Ala-OH (6.25 g, 27.4 mmoles) was dissolved in 30 mL of dioxane and was added to a solution of H-Lys(Boc)-OH (7.50 g, 30.4 mmoles) dissolved in a solution consisting of 30 mL of 1.0 N sodium hydroxide and triethylamine (2.12 mL, 15.0 mmoles). The reaction mixture was stirred overnight, then acidified with hydrochloric acid. Sufficient dry sodium chloride to nearly saturate the solution was added. The product was extracted into ethyl acetate and it was washed with 0.2 N hydrochloric acid prepared in saturated aqueous sodium chloride. The organic phase was dried over anhydrous sodium sulfate and filtered. Solvent was removed by evaporation. The product was crystallized from ethyl acetate:hexane to yield 7.3 g (mp 86°–89°).

Ac-Ala-Lys(Boc)-NH-CH[$(CH_2)_3$Br]$BO_2$-$C_{10}H_{16}$ was prepared by the procedure of Example 2 except that the product was purified by fractional crystallization from ethyl acetate. The product (1.13 g) obtained in the second and third crops exhibited a single spot on RP-TLC in methanol:water (85:15), with an Rf 0.51. The TLC plate was exposed to hydrochloric acid fumes wherein the resulting amine was detected after the addition of ninhydrin stain.

Ac-Ala-Lys(Boc)-NH-CH[$(CH_2)_3N_3$]$BO_2$-$C_{10}H_{16}$ was prepared from the corresponding alkyl bromide (1.95 g, 2.90 mmoles) by the procedure in Example 3 except that the product was purified by crystallizing it from ethyl acetate rather than LH-20 chromatography. Crude product (1.60 g) crystallized to yield 0.55 g mp 79°–84°) and 0.96 g of residue. The analysis of the crystalline product follows.

Analysis for $C_{30}H_{52}N_7O_7B$: Calculated: C=56.86%, H=8.29%, N=15.48%, and B=1.71%. Found: 56.76%, H=8.26%, N=15.89%, and B=1.65%.

Ac-Ala-Lys(Boc)-boroOrn-$C_{10}H_{16}$.benzene sulfonic acid was prepared from the corresponding alkyl azide (0.433 g, 0.683 mmoles) using the method described in Example 4. The catalyst and solvent were removed, then the product (0.45 g) was obtained by trituration with ether.

MS(FAB) for $C_{30}H_{54}N_9O_7B$: Calculated+H: 608.42. Found: 608.49.

Ac-Ala-Lys(Boc)-boroArg-$C_{10}H_{16}$.benzene sulfonic acid was prepared by reacting the corresponding boroOrnithine peptide with cyanamide using the method described in Example 5. The chromatography fractions containing the desired product were triturated with ether to yield 0.83 g as a white solid.

Analysis for $C_{37}H_{62}N_7O_{10}BS$: Calculated: C=55.00%, H=7.75%, N=12.14%, and B=1.34%. Found: C=54.09%, H=7.53%, N=12.22%, and B=1.34%.

EXAMPLE 14

Ac-Ala-Lys-boroArg-$C_{10}H_{16}$.2HCl

Ac-Ala-Lys(Boc)-boroArg-$C_{10}H_{16}$.benzene sulfonic acid (0.200 g, 0.248 mmoles) was deblocked by the procedure in Example 6. Following ion exchange, evaporation of solvent, drying in vacuo, and triturating with ether, 0.14 g of material were obtained.

MS(FAB) for $C_{26}H_{48}N_7O_5B$: Calculated+H: 550.39. Found: 550.42.

EXAMPLE 15

Boc-Leu-Gly-Leu-Ala-boroArg-$C_{10}H_{16}$.benzene sulfonic acid

Boc-Leu-Ala-OBzl was prepared by the procedure for dipeptide synthesis in Example 2. Boc-Leu-Ala-OBzl (23.7 g, 57.7 mmoles) was dissolved in 40 mL of anhydrous trifluoroacetic acid. After 15 min, excess trifluoroacetic acid was removed by evaporation and the residue was treated with ether to yield H-Leu-Ala-OBzl.trifluoroacetic acid as a crystalline product (22.8 g).

Analysis for $C_{18}H_{25}N_2O_5F_3$: Calculated: C=53.19%, H=6.21%, and N=6.89%. Found: C=53.37%, H=5.68%, and N=6.84%.

Boc-Gly-Leu-Ala-OBzl was prepared by coupling Boc-Gly-OH (5.70 g, 32.6 mmoles) to H-Leu-Ala-OBzl using the mixed anhydride procedure described in Example 2. The product (13.8 g) was obtained as an amorphous solid. Boc-Gly-Leu-Ala-OBzl was deblocked with trifluoroacetic acid by the procedure described for the preparation of H-Leu-Ala-OBzl except that the trifluoroacetate salt was soluble in ether. The preparation was dissolved in ethyl acetate and treated with anhydrous hydrogen chloride. The resulting product was precipitated by the addition of ether to yield 7.7 g of H-Gly-Leu-Ala-OBzl .HCl in a first crop.

Boc-Leu-Gly-Leu-Ala-OBzl was prepared by coupling Boc-Leu-OH (2.62 g, 10.5 mmoles) to H-Gly-Leu-Ala-OBzl using the mixed anhydride procedure described in Example 2. The resulting product was crystallized from ethyl acetate:hexane to yield 2.7 g (mp 95°-96°) in the first crop.

Analysis for $C_{29}H_{46}N_4O_7$: Calculated: C=61.89%, H=8.26%, and N=9.96. Found: C=62.00%, H=8.40%, and N=9.83%.

Boc-Leu-Gly-Leu-Ala-OH was prepared by the catalytic hydrogenation of the benzyl ester (2.6 g, 4.62 mmoles) by the procedure described in Example 2 to yield 2.1 g. The resulting product was crystallized from hot ethyl acetate to yield 1.4 g.

Analysis for $C_{22}H_{40}N_4O_7$: Calculated: C=55.90%, H=8.55%, and N=11.86%. Found: C=55.42%, H=8.47%, and N=11.73%.

Boc-Leu-Gly-Leu-Ala-NH-CH[$(CH_2)_3$Br]$BO_2$-$C_{10}H_{16}$ was prepared by coupling Boc-Leu-Gly-Leu-Ala-OH (1.40 g, 2.96 mmoles) to the amine from Example 1a. This was done using the procedure in Example 2 except that the chromatographic step was eliminated. The product crystallized from ethyl acetate:hexane to yield 1.17 g. TLC in methanol:chloroform (1:9) indicated a single spot Rf 0.68.

Analysis for $C_{36}H_{63}N_5O_8BrB$: Calculated: C=55.10%, H=8.11%, N=8.93%, and B=1.38%. Found: C=55.96%, H=8.30%, N=8.74%, and B=1.33%.

The corresponding azide was prepared by the procedure described in Example 3 in a yield of 97% and it was converted to Boc-Leu-Gly-Leu-Ala-boroOrn-$C_{10}H_{16}$ by the method described in Example 4. An analytical sample was prepared by precipitating the product with ether and then chromatographing it on LH-20, and reprecipitating it from chloroform with hexane.

MS(FAB) for $C_{36}H_{65}N_6O_8B$: Calculated+H: 721.50. Found: 721.55.

Boc-Leu-Gly-Leu-Ala-boroArg-$C_{10}H_{16}$.benzene sulfonic acid was prepared by the method described in Example 5. The corresponding boroOrnithine peptide (0.695 g, 0.791 mmoles) was reacted with 5 mL of a cyanamide solution (50 mg/mL) in absolute ethanol. The above mixture was chromatographed and triturated with ether, wherein 0.41 g of the desired product was obtained.

MS(FAB) for $C_{37}H_{67}N_8O_8B$: Calculated+H: 763.53. Found: 763.8.

EXAMPLE 16

H-Leu-Gly-Leu-Ala-boroArg-$C_{10}H_{16}$.HCl.benzene sulfonic acid

Boc-Leu-Gly-Leu-Ala-boroArg-$C_{10}H_{16}$.benzene sulfonic acid (Example 15, 0.050 g, 0.0543 mmoles) was reacted with 2 mL of 4 N hydrogen chloride in dioxane for 5 min at room temperature. Solvent and excess hydrogen chloride were removed by evaporation. The sample was dried over potassium hydroxide in vacuo, over night, and then triturated with ether to yield the product (46 mg) as a mixed salt.

MS(FAB) for $C_{32}H_{59}N_8O_6B$: Calculated+H: 663.47. Found: 663.50.

EXAMPLE 17

Bz-Glu(OBu)-Gly-boroArg-$C_{10}H_{16}$.benzene sulfonic acid

Bz-Glu(OBu)-Gly-NH-CH[$(CH_2)_3$Br]$BO_2$-$C_{10}H_{16}$ was prepared by coupling Bz-Glu(OBu)-Gly-OH to the amine according to the method described in Example 2. The corresponding azide was prepared by the method described in Example 3 and boroOrnithine peptide were prepared by the method described in Example 4.

MS(FAB) for $C_{32}H_{49}N_4O_7B$: Calculated+H: 613.38. Found: 613.60.

The final product was obtained by the method described in Example 5.

MS(FAB) for $C_{33}H_{51}N_6O_7B$: Calculated+H: 655.40. Found: 655.37. Analysis for $C_{39}H_{57}N_6O_{10}SB$: Calculated: C=57.62%, H=7.08%, N=10.34%, and B=1.33%. Found: C=57.43%, H=7.25%, N=9.91%, and B=1.23%.

EXAMPLE 18

Bz-Glu-Gly-boroArg-$C_{10}H_{16}$·benzene sulfonic acid

Bz-Glu(OBu)-Gly-boroArg-$C_{10}H_{16}$·benzene sulfonic acid (0.13 g, 0.16 mmoles) was dissolved in 5 mL of dioxane, benzene sulfonic acid (0.10 g, 0.66 mmoles) was added, and the solution was stirred overnight at room temperature. The solution was then concentrated to approximately 1 mL by evaporation and then it was triturated with ether to yield a solid (0.14 g). The material was chromatographed on a 2.5×50 cm column of LH-20 in methanol. Fractions containing the desired product were subjected to evaporation and the residue was triturated with ether to yield 53 mg of the desired product.

MS(FAB) for $C_{29}H_{43}N_6O_7B$: Calculated +H: 599.34. Found: 599.35+613.36 (unidentified).

EXAMPLE 18a

Bz-Glu-Gly-boroArg-$C_{10}H_{16}$·benzene sulfonic acid

Bz-Glu(OBu)-Gly-boroArg-$C_{10}H_{16}$·benzene sulfonic acid (Example 17, 0.20 g, 0.246 mmoles) was treated with anhydrous hydrogen chloride by the procedure described in Example 6 for 45 min. After the material was triturated with ether, NMR indicated that approximately 30% of the t-butyl protecting group was still present. The product was then reacted with anhydrous TFA for 45 min at room temperature. TFA was removed by evaporation and the residue was triturated with ether to yield 143 mg.

MS(FAB) for $C_{29}H_{43}N_6O_7B$: Calculated +H: 599.34. Found: 599.35.

EXAMPLE 19

Bz-Pro-Phe-boroArg-$C_{10}H_{16}$·benzene sulfonic acid

Bz-Pro-Phe-OH (mp 200°–201°) was prepared by the method described in Example 2 for dipeptide synthesis.

Analysis for $C_{21}H_{22}N_2O_4$: Calculated: C=68.82%, H=6.06%, and N=7.65%. Found: C=68.91%, H=6.09%, and N=7.47%.

Bz-Pro-Phe-NH-CH[$(CH_2)_3$Br]$BO_2$-$C_{10}H_{16}$ was prepared by coupling Bz-Pro-Phe-OH to the amine using the general method described in Example 2 except the chromatography step was eliminated. TLC in methanol:chloroform (1:9) indicated a major spot at Rf 0.72 and a trace at Rf 0.86.

MS(FAB) for $C_{35}H_{45}N_3O_5BBr$: Calculated+H: 678.27. Found: 677.95.

The alkyl halide was converted to the azide and to the boroOrnithine peptide by the procedures described in Examples 3 and 4.

MS(FAB) for (Bz-Pro-Phe-boroOrn-$C_{10}H_{16}$) $C_{35}H_{47}N_4O_5B$: Calculated+H: 615.37. Found: 615.42.

Bz-Pro-Phe-boroArg-$C_{10}H_{16}$·benzene sulfonic acid was prepared by the method described in Example 5.

MS(FAB) for $C_{36}H_{49}N_6O_5B$: Calculated+H: 657.39. Found: 657.13.

Analysis for $C_{42}H_{55}N_6O_8SB$: Calculated: C=61.90%, H=6.82%, N=10.31%, and B=1.33%. Found: C=60.16%, H=7.27%, N=9.79%, and B=1.44%.

EXAMPLE 20

Bz-Pro-Phe-boroArg-OH·HCl

Bz-Pro-Phe-boroArg-$C_{10}H_{16}$·benzene sulfonic acid (Compound of Example 19, 0.64 g, 0.79 mmoles) was dissolved in 4 mL of methylene chloride and cooled to −78°. It was added to flask containing 4 mL of 0.50 N boron trichloride, which had been prepared by diluting 1.0 N boron trichloride (Aldrich Chemical Co., Milwaukee, WI) 50% with dry methylene chloride, in a dry ice bath. The solution was stirred for 5 min at −78°, then the flask was transferred to a 0° ice bath where the solution was stirred for 15 min. Cold water (5 mL) was added slowly then the solution was diluted to 120 mL with 20% acetic acid. The organic phase which separated was removed and discarded. The aqueous phase was applied to a 20 mL column of SP-Sephedex ™ which was equilibrated with 20% acetic acid. The column was washed with approximately 150 mL of 20% acetic acid then subjected to a linear gradient from 200 mL of 20% acetic acid to 200 mL of 20% acetic acid containing 0.30 N hydrochloric acid. The product eluted when the concentration of hydrochloric acid was between 0.08 and 0.15 N. The desired product (0.19 g) was obtained after evaporating the solvent, drying the residue in vacuo, and triturating it with ether.

MS(FAB) for $C_{26}H_{35}N_6O_5B$: Calculated +H: 523.29. Found: 579.34 (unidentified).

Analysis for $C_{26}H_{36}N_6O_5ClB$. Calculated: C=53.29%, H=6.55%, N=14.34%, and B=1.84%. Found C=53.27%, H=6.58%, N=13.25%, and B=1.89%.

Esterification of the product with pinanediol as described in Example 8a gave a product whose NMR and MS properties were consistent with the starting ester of Example 19.

MS(FAB) for $C_{34}H_{49}N_6O_5B$: Calculated+H: 657.40. Found: 657.39.

EXAMPLE 21

Bz-Pro-Phe-boroArg-F·hydrogen chloride

Bz-Pro-Phe-NH-CH[$(CH_2)_2$NH-C(NH)$NH_2$]$BF_2$·HCl

Bz-Pro-Phe-boroArg-F was prepared by a modification of the procedure described by Kinder et al., J. Med. Chem., 28: 1917–1925, (1985). Free boronic acid (Compound of Example 20, 0.100 g, 0.179 mmoles) was dissolved in 2 mL of water. To it, 0.040 mL of 48% hydrofluoric acid was added at room temperature. A gummy precipitant formed almost instantly. The reaction was stirred for 10 min, then the mixture was frozen and excess hydrofluric acid and water were removed in vacuo. The residue was dissolved in methanol, concentrated, and triturated with ether. A yield of 0.093 g was obtained.

MS(FAB) for $C_{26}H_{33}N_6O_3BF_2$: Calculated+H: 527.29. Found: 527.31 and additional masses characteristic of the free boronic acid. Analysis for $C_{26}H_{34}N_6O_3BF_2Cl·H_2O$ Calculated: C=53.47%, H=6.25%, N=14.47%, B=1.86%, and F=6.54%. Found: C=54.00%, H=6.40%, N=13.48%, B=1.95%, and F=7.06%.

EXAMPLE 22

Boc-(D)Phe-Pro-boroIrg-$C_{10}H_{16}$·HBr

BoroIrg- is the abbreviation for —NH—CH[$(CH_2)_3$S—C(NH)$NH_2$]$BO_2$— in which the isothiouronium group replaces the guanidino of boroArginine. Boc-(D)Phe-Pro-NH—CH[$(CH_2)_3$Br]$BO_2$-$C_{10}H_{16}$ (Compound of Example 2, 1.00 g, 1.61 mmoles) was dissolved in 4 mL of absolute ethanol and thiourea (0.37 g, 4.82 mmoles) was added. The mixture was stirred overnight at room temperature. The solution was concentrated and the residue was triturated with ether to yield 0.58 g of solid. The resulting solid was chromatographed on a 2.5 ×50 cm column of LH-20 in methanol. Pooled fractions containing the desired product were subjected to evaporation to yield 0.26 g of product. The sample was triturated with ether to yield 0.150 g of an amorphous solid.

MS(FAB) for $C_{34}H_{53}N_5O_6BS$: Calculated+H: 670.38. Found: 670.39. Analysis for $C_{34}H_{53}N_5O_6SBrB$. Calculated: C=54.40%, H=7.13%, N=9.33%, and B=1.44%. Found: C=54.10%, H=7.39%, N=9.27%, and B=1.47%.

The ether soluble residue obtained from this reaction consisted mainly of starting material which was converted to isothiouronium salt by longer reaction periods.

This general procedure was used to prepare other isothiouronium salts except in some cases a 4-fold excess of thiourea and 3-4 day reaction times were used.

EXAMPLE 23

H-(D)Phe-Pro-boroIrg-$C_{10}H_{16}$.HBr,HCl

Boc-(D)Phe-Pro-boroIrg-$C_{10}H_{16}$.HBr (Compound of Example 22, 0.050 g, 0.067 mmoles) was reacted with 1 mL of 4 N hydrogen chloride in dioxane for 15 min at room temperature. Solvent was evaporated and the residue was triturated with ether to yield 0.040 g of a white solid.

MS(FAB) for $C_{29}H_{45}N_5O_4SB$: Calculated+H: 571.29. Found: 570.47.

EXAMPLE 24

Ac-Ala-Lys(Boc)-boroIrg-$C_{10}H_{16}$.HBr

Ac-Ala-Lys(Boc)—NH—CH[$(CH_2)_3Br$]$BO_2$-$C_{10}H_{16}$ (from Example 13, 0.700 g, 1.04 mmoles) was reacted with thiourea (0.320 g, 4.00 mmoles) for 4 days in 4 mL of absolute ethanol. The product was purified by the procedure described in Example 22. Following chromatography, 0.28 g of the desired product were obtained. Trituration with ether yielded 0.173 g of the product as an amorphous white solid.

MS(FAB) for $C_{31}H_{55}N_6O_7SB$: Calculated+H: 667.8. Found: 667. Analysis for $C_{31}H_{56}N_6O_7SBrB$: Calculated: C=49.79%, H=7.56%, N=11.24%, and B=1.44%. Found: C=49.20%, H=7.62%, N=11.31%, and B=1.36%.

EXAMPLE 25

Ac-Ala-Lys-boroIrg-$C_{10}H_{16}$.2HBr

Ac-Ala-Lys(Boc)-boroIrg-$C_{10}H_{16}$.HBr (the compound of Example 24, 0.050 g, 0.067 mmoles) was dissolved in 1 mL of methanol and hydrogen bromide gas was bubbled though the solution of 10 min. Solvent was removed by evaporation and the residue was triturated with ether to yield the desired product as a solid (49 mg).

MS(FAB) for $C_{36}H_{47}N_6O_5SB$: Calculated+H: 567.35. Found: 567.41.

EXAMPLE 26

Ac-Phe-boroIrg-$C_{10}H_{16}$.HBr

Ac-Phe-NH—CH[$(CH_2)_3Br$]$BO_2$-$C_{10}H_{16}$ (from Example 9, 1.00 g, 2.41 mmoles) was reacted with a 3-fold excess of thiourea in 5 mL of absolute thanol following the procedure described in Example 22. The product (0.284 g) was obtained as a white amorphous solid. Additional product was obtained by again reacting any remaining ether soluble material with thiourea and repeating the purification procedure.

MS(FAB) for $C_{26}H_{39}N_4O_4SB$: Calculated +H: 515.29. Found: 515.29. Analysis for $C_{26}H_{39}N_4O_4SB$. Calculated: C=52.44%, H=6.79%, N=9.41%, and B=1.82%. Found: C=52.83%, H=6.89%, N=8.47%, and B=1.85%.

EXAMPLE 27

Bz-Pro-Phe-boroIrg-$C_{10}H_{16}$.HBr

Bz-Pro-Phe-NH-CH[$(CH_2)_3Br$]$BO_2C_{10}H_{16}$ (product from Example 19, 0.500 g, 0.737 mmoles) was used to prepare the product of this example by following the procedure described in Example 22. Product (0.358 g) was obtained as a white solid.

MS(FAB) for $C_{36}H_{48}N_5O_5SB$: Calculated +H: 674.35. Found: 674.27. Analysis for $C_{36}H_{49}N_5O_5SBBr$. Calculated: C=57.29%, H=6.56%, N=9.28%, and B=1.43%. Found: C=57.46%, H=6.45%, N=8.78%, and B=1.38%

EXAMPLE 28

Boc-Leu-Gly-Leu-Ala-boroIrg-$C_{10}H_{16}$.HBr

Boc-Leu-Gly-Leu-Ala-NH-CH[$(CH_2)_3Br$]$BO_2$-$C_{10}H_{16}$ (product from Example 15, 0.770 g, 0.980 mmoles) was used to prepared the isothiouronium analog of this example using the procedure described in Example 22. Following chromatography of the reaction products, the final product (0.400 g) was obtained as a white solid by trituration with hexane.

MS(FAB) for $C_{37}H_{66}N_7O_8SB$: Calculated:+H: 780.48. Found: 780.52. Analysis for $C_{37}H_{67}N_5O_8SBrB$. Calculated: C=51.62%, H=7.86%, N=11.39%, and B=1.26%. Found: C=51.03%, H=7.86%, N=11.14%, and B=1.18%.

EXAMPLE 29

H-Leu-Gly-Leu-Ala-boroIrg-$C_{10}H_{16}$.2HBr

Boc-Leu-Gly-Leu-Ala-boroIrg-$C_{10}H_{16}$.HBr (compound of Example 28, 0.100 g, 0.12 mmoles) was dissolved in 1 mL of methanol and 1 mL of 0.7 N hydrogen bromide in methylene chloride was added. The mixture was stirred for 15 min at room temperature. Solvent and excess hydrogen bromide were removed by evaporation and the residue was triturated with ether to yield the desired product in almost quantitative yield.

MS(FAB) for $C_{32}H_{58}N_7O_6SB$: Calculated +H: 680.43. Found: 680.50.

EXAMPLE 30

Bz-Glu(OBu)-Gly-boroIrg-$C_{10}H_{16}$.HBr

Bz-Glu(OBu)-Gly-NH[$(CH_2)_3Br$]$BO_2$-$C_{10}H_{16}$ (product from Example 17, 0.293 g, 0.433 mmoles) was used to prepare the isothiouronium analog (0.220 g) using the procedure described in Example 22.

MS(FAB) for $C_{33}H_{50}N_5O_7SB$: Calculated+H: 672.36. Found: 672.3. Analysis for $C_{33}H_{51}N_5O_7SBBr$: Calculated: C=52.66%, H=6.84%, N=9.31%, and B=1.44%. Found: C=52.38%, H=6.76%, N=8.81%, and B=1.46%.

EXAMPLE 31

Bz-Glu-Gly-boroIrg-$C_{10}H_{16}$.HBr

Bz-Glu(OBu)-Gly-boroIrg-$C_{10}H_{16}$.HBr (the product of Example 30, 0.050 g, 0.066 mmoles) was dissolved in 1 mL of TFA and stirred for 1 h at room temperature. Hydrogen bromide in methylene chloride (0.35 mmoles) was added and the liquid of the resulting solution was evaporated. The residue was triturated with ether to yield 47 mg.

MS(FAB) for $C_{29}H_{42}N_5O_7SB$: Calculated+H: 616.30. Found: 616.34.

EXAMPLE 32

Boc-(D)Phe-Phe-boroIrg-$C_{10}H_{16}$.HBr

Boc-(D)Phe-Phe-NH-CH[(CH$_{:}$)$_3$Br]BO$_2$-$C_{10}H_{16}$ (compound from Example 11, 1.50 g, 2.07 mmoles) was used to prepare the isothiouronium analog (0.90 g) using the procedure described in Example 22.

MS(FAB) for $C_{38}H_{54}N_5O_6SB$: Calculated+H: 719.84. Found: 720. Analysis for $C_{38}H_{55}N_5O_6SBBr$: Calculated: C=56.99%, H=6.94%, N=8.75%, and B=1.35%. Found C=55.89%, H=6.87%, N=8.59%, and B=1.18%.

EXAMPLE 33

H-(D)Phe-Phe-boroIrg-$C_{10}H_{16}$.2HBr

Boc-(D)Phe-Phe-boroIrg-$C_{10}H_{10}$.HBr (compound of Example 20, 0.20 g, 0.25 mmoles) was reacted with hydrogen bromide by the procedure described in Example 29 to yield 188 mg of the desired product.

MS(FAB) for $C_{33}H_{46}N_5O_5SB$: Calculated+H: 620.34. Found: 620.40.

EXAMPLE 34

Z-PheGly-Gly-boroIrg-$C_{10}H_{16}$.HBr

Z-Phe-Gly-Gly-NH-CH[(CH$_2$)$_3$Br]BO$_2$-$C_{10}H_{12}$ was prepared by coupling Z-Phe-Gly-Gly-OH to the amine (Example 1a) using the procedure described in Example 2.

Analysis for $C_{35}H_{46}N_4O_7BBr$: Calculated: C=57.93%, H=6.40%, N=7.72%, and B=1.49%. Found: C=58.42%, H=6.83%, N=7.74%, and B=1.96%.

The alkyl halide (1.00 g, 1.38 mmoles) was converted to the isothiouronium analog by the method in Example 22 to yield product (0.87 g) as a white amorphous solid.

MS(FAB) for $C_{36}H_{49}N_6O_7SB$: Calculated+H: 721.36. Found: 721.32. Analysis for $C_{36}H_{50}N_6O_7SBBr$: Calculated: C=54.00%, H=6.31%, N=10.50%, and B=1.35%. Found: C=53.17%, H=6.50%, N=10.03%, and B=1.25%.

EXAMPLE 35

Boc-Ala-Phe-(D,L)boroIrg-$C_6H_{12}$.HBr

Boc-Ala-Phe-OMe was prepared using the mixed anhydride procedure described in Example 2.

Analysis for $C_{18}H_{26}N_2O_5$: Calculated: C=61.70%, H=7.48%, N=7.99%. Found: C=61.51%, H=7.56%, N=7.92%.

The methyl ester was hydrolyzed with base to yield Boc-Ala-Phe-OH in a yield of 56%. Boc-Ala-Phe-NH—CH[(CH$_2$)$_3$Br]BO$_2$-$C_6H_{12}$ was prepared by coupling Boc-Ala-Phe-OH to NH$_2$—CH[(CH$_2$)$_3$Br]BO$_2$-$C_6H_{12}$.HCl (Example 1b) using the method described in Example 2, except LH-20 chromatography was not used.

Boc-Ala-Phe-NH—CH[(CH$_2$)$_3$Br]BO$_2$-$C_6H_{12}$ (1.00 g, 1.72 mmoles) was reacted with thiourea using the procedure described in Example 22 to yield the isothiouronium analog (0.485 g) as a white solid.

MS(FAB) for $C_{28}H_{46}N_5O_6SB$: Calculated +H: 592.33. Found: 592.60. Analysis for $C_{28}H_{47}N_5O_6SBBr$: Calculated: C=50.00%, H=7.06%, N=10.41%, and B=1.61%. Found: C=49.50%, H=7.24%, N=10.22%, and B=1.41%.

EXAMPLE 36

H-Ala-Phe-(D,L)boroIrg-$C_6H_{12}$.2HBr

Boc-Ala-Phe-boroIrg-$C_6H_{12}$.HBr (Example 35, by the procedure described in Example 29 to yield the desired product in almost quantitative yield.

MS(FAB) for $C_{23}H_{36}N_5O_6SB$: Calculated+H: 492.28. Found: 492.26.

EXAMPLE 37

Boc-Ala-Phe-(D,L)boroHomoIrg-$C_6H_{12}$.HBr

Boc-Ala-Phe-NH—CH[(CH$_2$)$_4$—S—C(NH)NH$_2$]BO$_2$-$C_6H_{12}$.HBr

Boc-Ala-Phe-OH (from Example 35) was coupled to the amine (Example 1d) to yield Boc-Ala-Phe-NH—CH[(CH$_2$)$_4$Br]BO$_2$-$C_6H_{12}$. The procedure in Example 2 was used except the LH-20 chromatography step was not needed for purification. An analytical sample was obtained by chromatography on silica gel using ethyl acetate as an eluent.

MS(FAB) for $C_{28}H_{45}N_3O_6BrB$: Calculated+H: 610.27. Found: 610.24. Analysis for $C_{28}H_{45}N_3O_6BrB$. Calculated C=55.19%, H=7.28%, N=6.90%, Br=13.11%, and B=1.78%. Found: C=55.30%, H=7.39%, N=6.40, Br=12.07%, and B=1.95%.

The alkyl bromide (0.537 g, 0.883 mmoles) was reacted with thiourea using the procedure in Example 22. The product (0.23 g) was obtained as an amorphous white solid after trituration with ether.

MS(FAB) for $C_{29}H_{48}N_5O_6S$: Calculated+H: 606.35. Found: 606.38. Analysis for $C_{29}H_{49}N_5O_6SBBr$. Calculated: C=50.73%, H=7.21%, N=10.20%, and B=1.57%. Found: C=50.22%, H=7.46%, N=9.74%, and B=1.55%.

EXAMPLE 38

H-Ala-Phe-(D,L)boroHomoIrg-$C_6H_{12}$.2HBr

Boc-Ala-Phe-(D,L)boroHomoIrg-$C_6H_{12}$.HBr (compound of Example 37, 0.050 g, 0.073 mmoles) was allowed to react with hydrogen bromide by the procedure descibed in Example 29 to yield 44 mg of the desired product.

MS(FAB) for $C_{24}H_{40}N_5O_4SB$: Calculated+H: 506.30. Found: 506.39.

EXAMPLE 39

Boc-Ala-Phe-(D,L)boroLys-$C_6H_{12}$.HCl

Boc-Ala-Phe-NH—CH[(CH$_2$)$_4$NH$_2$]BO$_2$-$C_6H_{12}$.benzene sulfonic acid

Boc-Ala-Phe-NH—CH[(CH$_2$)$_4$Br]BO$_2$-$C_6H_{12}$ (from Example 35) was converted to the alkyl azide using the procedure in Example 3 except the LH-20 chromatography step was not needed for purification. The azide was hydrogenated using the method described in Example 4 except 2 equivalents of benzene sulfonic acid were used and the hydrogenation time was 2 h to yield the final product in a yield of 40% (mp 154°-160°, dec).

MS(FAB) for $C_{28}H_{46}N_4O_6B$: Calculated+H: 547.38. Found: 547.43.

EXAMPLE 40

H-A]a-Phe-(D,L)boroLys-$C_6H_{12}$.TFA.benzene sulfonic acid

Boc-Ala-Phe-(D,L)boroLys-$C_6H_{12}$.benzene sulfonic acid (compound of Example 39) was reacted with trifluoroacetic acid for 1 hr at room temperature. Solvent was evaporated and the residue was triturated with ether to yield a solid.

MS(FAB) for $C_{23}H_{39}N_4O_4B$: Calculated+H: 447.31. Found: 447.31. Anal. for $C_{31}H_{46}N_4O_9SF_3B.2H_2O$ Calculated C=49.34%, H=6.68%, N=7.42%, and B=1.43%. Found: C=49.26%, H=5.94%, N=7.12%, and B=1.34%.

EXAMPLE 41

Boc-(D)Val-Leu-boroLys-$C_6H_{12}$.benzene sulfonic acid

Boc-(D)Val-Leu-OH was prepared by the method described in Example 2. The benzyl ester was obtained in a yield of 76%.

MS(FAB) for $C_{23}H_{36}N_2O_5$: Calculated+H: 421.27. Found: 421.38.

Following hydrogenation, the free acid was obtained in a yield of 100% as a white crystalline solid.

Analysis for $C_{16}H_{36}N_2O_5$: Calculated: C=59.34%, H=8.87%, and N=8.50%. Found: C=59.34%, H=8.87%, and N=8.50%.

Boc-(D)Val-Leu-OH was coupled to the amine (Example 1d) using the method described in Example 37 for the coupling of Boc-Ala-Phe-OH to yield Boc-(D)Val-Leu-NH—CH[$(CH_2)_3Br$]$BO_2$-$C_6H_{12}$ in a yield of 97%.

MS(FAB) for $C_{27}H_{51}N_3O_6BBr$: Calculated+H: 604.31. Found 604.31.

The alkyl bromide was converted to the corresponding azide in a yield of 85% by the method described in Example 3, and the azide was hydrogenated by the method described in Example 39 to yield the final product as a white solid in a yield of 62%.

MS(FAB) for $C_{27}H_{53}N_4O_6B$: Calculated+H: 541.41. Found: 541.46. Analysis $C_{33}H_{59}N_4O_9SB.1.5\ H_2O$: Calculated: C=54.62%, H=8.61%, N=7.73%, and B=1.49%. Found: C=54.58%, H=8.59%, N=7.92%, and B=1.98%

EXAMPLE 42

Ac-Phe-boroLys-$C_6H_{12}$.benzene sulfonic acid

Example 42 was prepared according to the procedure described in Example 39.

Ac-Phe-NH-CH[$(CH_2)_3Br$]$BO_2$-$C_6H_{12}$ was prepared in a yield of 72%.

MS(FAB) for $C_{22}H_{34}N_2O_4BBr$: Calculated+H: 481.00. Found: 481.21.

The azide was obtained in a yield of 57%. The final product was obtained in a yield of 50%.

MS(FAB) for $C_{22}H_{27}N_3O_4B$: Calculated:+H: 418.29. Analysis for $C_{29}H_{42}N_3O_7SB.H_2O$: Calculated: C=56.66%, H=7.47%, N=7.08%, and B=1.82%. Found: C=56.88%, H=7.43%, N=7.22%, and B=1.53%.

EXAMPLE 43

Bz-(D,L)boroIrg-$C_6H_{12}$.HBr

Bz-(D,L)NH-CH[$(CH_2)_3Br$]$BO_2$-$C_6H_{12}$ was prepared by reacting the amine (Example 1b, 5.0 g, 15.9 mmoles) with an equivalent of benzoyl chloride and two equivalents of sodium bicarbonate in a mixture consisting of 4 mL of dioxane and 4 mL of water at 0°. After initially mixing the reagents, the reaction was diluted with 6 mL of 50% dioxane:water and it was allowed to warm to room temperature. The reaction mixture was stirred approximately 30 min at room temperature and then the product was extracted into ethyl acetate and washed with water, 0.2 N hydrochloric acid, 5% aqueous sodium bicarbonate, and saturated aqueous sodium chloride. The organic phase was dried over anhydrous sodium sulfate, filtered, and evaporated to yield a crystalline product. After isolation and washing with ethyl acetate, 3.26 g of compound (mp 176°-177°) were obtained.

Analysis for $C_{17}H_{25}NO_3BrB$: Calculated: C=53.44%, H=6.59%, N=3.67%, and B=2.83%. Found: C=54.50%, H=6.76%, N=3.68%, and B=2.84%.

The alkyl halide (1.00 g, 2.62 mmoles) was converted to corresponding isothiouronium salt by the procedure described in Example 22. The product, 0.84 g, was obtained as a white solid.

MS(FAB) for $C_{18}H_{28}N_3O_3SB$: Calculated+H: 378.20. Found: 378.21. Analysis for $C_{18}H_{29}N_3O_3SBBr$: Calculated: C=47.18%, H=6.38%, N=9.17%, and B=2.36%. Found: C=46.11%, H=6.71%, N=8.97%, and B=2.22%.

EXAMPLE 44

Bz-(D,L)boroArg-$C_6H_{12}$.benzene sulfonic acid

The alkyl halide (Example 43, 2.0 g, 5.25 mmoles) was converted to 0.97 g of the azide (mp 138°-139°) using the procedure in Example 3. The azide was converted to Bz-boroOrn-$C_6H_{12}$.benzene sulfonic acid in almost quantitative yield using the procedure in Example 4.

MS(FAB) for $C_{18}H_{27}N_2O_3B$: Calculated+H: 319.22. Found 319.26.

Bz-boroOrn-$C_6H_{12}$.benzene sulfonic acid (0.90 g, 1.84mmoles) was allowed to react with cyanamide using the procedure in Example 5 to yield 0.65 g of crystalline product (mp 242°-244°).

FAB(MS) for $C_{18}H_{29}N_4O_3B$: Calculated+H: 361.24. Found: 361.24.

Analysis for $C_{24}H_{35}N_4O_6SB$: Calculated: C=55.59%, H=6.82%, N=10.81%, and B=2.08%. Found: C=54.60%, H=6.70%, N=11.24%, and B=1.87%.

EXAMPLE 45

Ac-Leu-Thr(OBu)-boroArg-$C_{10}H_{16}$. benzene sulfonic acid

Ac-Leu-Thr(OBu)-OH was prepared by coupling Ac-Leu-OSu to H-Thr(OBu)-OH using the procedure in Example 13 for dipeptide synthesis except the final product was obtained as an amorphous white solid after chromatography on LH-20. Ac-Leu-Thr(OBu)-OH (3.29 g, 9.90 mmoles) was coupled to the amine (Example la) using the mixed anhydride procedure in Example 2 except the LH-20 chromatography step was not needed. Ac-Leu-Thr(OBu)-NH—CH[$(CH_2)_3Br$]$BO_2$-$C_{10}H_{16}$was obtained as an amorphous white solid, 5.39 g. The alkyl halide was converted to the corresponding azide in a yield of 82% using the procedure in Example 3 except a chromatography step was needed for further purification. The azide (3.88 g, 6.42 mmoles) was hydrogenated by the procedure in Example 4. The product, Ac-Leu-Thr(OBu)-boroOrn-$C_{10}H_{16}$.benzene sulfonic acid, was obtained in a yield of 74% after chromatography of the product on LH-20 and trituration with ether.

MS(FAB) for $C_{30}H_{55}N_4O_6B$: Calculated+H: 579.43. Found: 579.48.

The boroOrnithine peptide was converted to the final product in a yield of 86% by the procedure in Example 5.

MS(FAB) for $C_{31}H_{57}N_6O_6B$: Calculated+H: 621.45. Found: 621.50. Analysis for $C_{37}H_{63}N_6SO_9B$: Calculated: C=57.05%, H=8.17%, N=10.79%, B=1.39%. Found: C=56.47%, H=8.01%, N=10.93%, and B=1.34%.

EXAMPLE 46

Ac-Leu-Thr-boroArg-$C_{10}H_{16}$·benzene sulfonic acid

Ac-Leu-Thr(OBu)-boroArg-$C_{10}H_{16}$·benzene sulfonic acid (Example 45, 0.200 g, 0.257 mmoles) was dissolved in a mixture of 2 mL of methylene chloride and mL of 4 N HCl:dioxane and was allowed to stir for 30 min at room temperature. Solvent was evaporated and the residue was dried under high vacuum. The desired product was obtained as a white solid in a yield of 97% by triturating with ether.

MS(FAB) for $C_{27}H_{49}N_6O_6B$: Calculated+H: 565.39. Found: 565.48.

EXAMPLE 47

Ac-Lys(Boc)-Pro-boroArg-$C_{10}H_{16}$·benzene sulfonic acid

Ac-Lys(Boc)-Pro-OH was prepared by the methods described in Example 13. It was obtained as a white solid (mp 160°-161.5°) after crystallization from ethyl acetate. Ac-Lys(Boc)-Pro-OH (3.15 g, 8.18 mmoles) was coupled to the amine (Example 1a) using the procedure in Example 2. The product, 5.8 g, was used without further purification. It was converted to the azide in a yield of 73% by the method in Example 3 after chromatography on LH-20. Hydrogenation by the method in Example 4, chromatography on LH-20, and trituration of the sample with ether gave Ac-Lys(Boc)-Pro-boroOrn-$C_{10}H_{16}$·benzene sulfonic acid in a yield of 81%.

MS(FAB) for $C_{32}H_{55}N_5O_7B$: Calculated+H: 634.43. Found: 634.46.

The boroOrnithine peptide (2.0 g, 2.53 mmoles) reacted with cyanamide by the procedure in Example 5 to yield 1.8 g of the desired product as a white solid.

MS(FAB) for $C_{33}H_{57}N_7O_7B$: Calculated+H: 676.46. Found: 676.41. Analysis for $C_{39}H_{63}N_7O_7BS$: Calculated: C=56.23%, H=7.64%, N=11.77%, and B=1.30%. Found: 56.06%, H=7.48%, N=11.75%, and B=1.22%.

EXAMPLE 48

Ac-Lys-Pro-boroArg-$C_{10}H_{16}$·2HCl

Ac-Lys(Boc)-Pro-boroArg-$C_{10}H_{16}$·benzene sulfonic acid (Example 47, 0.30 g, 0.360 mmoles) was reacted with a 50:50 mixture of glacial acetic and 4 N HCl:dioxane for 15 min at room temperature. Solvent was evaporated and the residue was dried in vacuo. The residue was dissolved in water and passed through a 5 mL column of AG1-X8 (Cl$^-$ form). The sample was evaporated and the residue was triturated with ether to yield the desired product as a white solid (230 mg).

MS(FAB) for $C_{28}H_{49}H_7O_5B$: Calculated+H: 576.40. Found: 576.45.

EXAMPLE 49

Ac-Ala-Glu(OBu)boroArg-$C_{10}H_{16}$·benzene sulfonic acid

Ac-Ala-Glu(OBu)-OH was prepared by coupling Ac-Ala-OSu to H-Glu(OBu)-OH using the procedure in Example 13. The product crystallized from ethyl acetate:hexane (mp 147.5°-148°). Analysis for $C_{14}H_{24}N_2O_6$: Calculated: C=53.14%, H=7.66%, and N=8.85%. Found: C=53.28%, H=7.53%, and N=9.08%.

Ac-Ala-Glu(OBu)-NH-CH[$(CH_2)_3$BrBO$_2$-$C_{10}H_{16}$ was prepared by the method in Example 2 except chloroform was used instead of ethyl acetate for the organic phase during the initial workup of the reaction and chromatography on LH-20 was not used. The desired product was obtained in a yield of 87% as partially crystalline solid after evaporation of the organic phase. The alkyl bromide was converted to the azide by the procedure in Example 3. The desired product (mp 163.5°-166°) was obtained in a yield of 50% by crystallizing the crude reaction product from chloroform.

Analysis for $C_{28}H_{47}N_6O_7B$: Calculated: C=53.51%, H=7.55%, N=6.69% and B=1.73%. Found C=55.51%, H=7.50%, N=6.50%, and B=1.66%.

The boroOrnithine peptide was prepared by the method in Example 4 to yield the desired product in a yield of 79%.

MS(FAB) for $C_{28}H_{49}N_4O_7B$: Calculated+H: 565.38. Found: 565.51.

The final product was obtained as a white amorphous solid in a yield of 70% using the procedure in Example 5.

MS(FAB) for $C_{29}H_{51}N_6O_7B$: Calculated+H: 607.40. Found: 607.41. Analysis for $C_{35}H_{57}N_6O_{10}BS$: Calculated: C=54.96%, H=7.53%, N=10.99%, and B=1.41%. Found: C=54.36%, H=7.71%, N=11.27% and B=1.21%

EXAMPLE 50

Ac-Ala-Glu-boroArg-$C_{10}H_{16}$·benzene sulfonic acid

Ac-Ala-Glu(Bu)-boroArg-$C_{10}H_{16}$·benzene sulfonic acid (Example 49, 0.10 g, 0.131 mmoles) was dissolved in 10 mL of acetic acid and anhydrous HCl was bubbled through the solution for 20 min. The solution was stirred at room temperature for 1.5 h and solvent was evaporated to yield an oil. The desired product was obtained as a white solid (82 mg) after drying in vacuo and trituration with ether.

MS(FAB) for $C_{25}H_{43}N_6O_7B$: Calculated+H: 551.34. Found: 551.41.

The following compounds were also prepared using substantially the same procedures as in Examples and 40 above:

Boc-Val-Val-boroLys-$C_6H_{12}$·BSA;
H-Val-Val-boroLys-$C_6H_{12}$·BSA.TFA;
Boc-(D)Phe-Phe-boroLys-$C_6H_{12}$·BSA;
H-(D)Phe-Phe-boroLys-$C_6H_{12}$·BSA.TFA
Boc-Glu-Phe-boroLys-$C_6H_{12}$·BSA
PyroGlu-Phe-boroLys-$C_6H_{12}$·BSA

BIOLOGICAL EXAMPLES

In the following examples, μ denotes micro.

EXAMPLES 51-71

Inhibition of Human Plasma Kallikrein

Human plasma kallikrein was obtained from Protogen AG (Switzerland). The specific activity as described by the supplier is 15 units per mg. A unit is defined as the quantity of enzyme required to hydrolyze 1 μmole of substrate, H-(D)Pro-Phe-Arg-p-nitroanilide (Kabi S2302), per min at a substrate concentration of 0.50 mM at 25° in 50 mM potassium phosphate buffer, pH 8.0.

A stock solution of enzyme (1 unit/mL) was prepared in 50% glycerol-0.10M sodium phosphate buffer, pH 7.5, containing 0.20 M sodium chloride and 0.1% PEG 6000 (polyethylene glycol). In standard assays, 10 μL of the stock kallikrein solution were added to 990 μL of a solution consisting of 0.20 mM S2302 in 0.10 mM sodium phosphate buffer, pH 7.5, containing 0.20 M sodium chloride and 0.1% PEG at 25°. The effect of inhibitors were evaluated by monitoring enzymatic activity determined by measuring the increase in absorbance at 405 nm with time both in the presence and absence of inhibitors. Table 1 shows inhibitor levels and the activity remaining measured in the time interval from 10 to 20 min following initiation of the reaction. Activity of the controls were $0.0092 \pm 0.0095$ min$^{-1}$.

TABLE 1

Inhibition of Human Plasma Kalikrein

| Ex | Inhibitor | Conc. (nM) | Percent Activity |
|---|---|---|---|
| 51 | Boc—(D)Phe—Phe—boroIrg—$C_{10}H_{16}$.HBr | 10 | 2 |
| 52 | H—(D)Phe—Phe—boroArg—$C_{10}H_{16}$.2HCl | 10 | 2.6 |
| 53 | Boc—(D)Phe—Phe—boroArg—$C_{10}H_{16}$.BSA | 10 | 5.2 |
| 54 | Boc—Ala—Phe—(D,L)boroIrg—$C_6H_{12}$.HBr | 10 | 15 |
| 55 | Bz—Pro—Phe—boroArg—$C_{10}H_{16}$.BSA | 10 | 15 |
| 56 | Ba—Pro—Phe—boroArg—OH.HCl | 10 | 16 |
| 57 | Bz—Pro—Phe—boroArg—F | 10 | 18 |
| 58 | Boc—Leu—Gly—Leu—Ala—boroArg—$C_{10}H_{16}$.BSA | 10 | 30 |
| 59 | Ac—Ala—Lys(Boc)—boroArg—$C_{10}H_{16}$.BSA | 10 | 34 |
| 60 | Ac—Phe—boroArg—$C_{10}H_{16}$.HCl | 10 | 48 |
| 61 | Ac—(D)—Phe—Pro—boroArg—$C_{10}H_{16}$.HCl | 10 | 56 |
| 62 | H—(D)Phe—Pro—boroArg—$C_{10}H_{16}$2.HCl | 10 | 61 |
| 63 | Ac—Ala—Lys(Boc)—boroIrg—$C_{10}H_{16}$.HBr | 50 | 1.4 |
| 64 | Bz—Glu(OBu)—Gly—boroArg—$C_{10}H_{16}$.BSA | 50 | 11 |
| 65 | Ac—Phe—boroIrg—$C_{10}H_{16}$.HBr | 50 | 17 |
| 66 | Ba—Glu—Gly—boroArg—$C_{10}H_{16}$.BSA | 50 | 39 |
| 67 | Ac—Ala—Lys—boroArg—$C_{10}H_{16}$.2HCl | 50 | 39 |
| 68 | Boc—Ala—Phe—(D,L)borohomoIrg—$C_6H_{12}$.HBr | 100 | 38 |
| 69 | Boc—Ala—Phe—(D,L)boroLys—$C_6H_{12}$.HCl | 1000 | 17 |
| 70 | Boc—(D)Phe—Phe—boroOrn—$C_{10}H_{16}$.BSA | 10000 | 39 |
| 71 | Boc—(D)Phe—Pro—boroOrn—$C_{10}H_{16}$.BSA | 10000 | 100 |

EXAMPLES 72-110

Inhibition of Thrombin (Esterase Activity)

Human thrombin (specific activity 2345 NIH units/mg) was obtained from R.Q.P. Laboratories, South Bend, IN) (Lot HT102). A stock solution of thrombin was prepared in 0.010M PIPES Buffer, pH 6.0, containing 0.75 M sodium chloride. Assays of thrombin were run according to the procedure of Green and Shaw, Anal. Biochem., 93; 223 (1979), in sodium phosphate buffer, pH 7.5, containing 0.20 M sodium chloride and 0.1% PEG 6000. The initial concentration of substrate was 0.10 mM and the concentration of thrombin was 1.0 nM (based on weight). Table 2 shows inhibitor levels and the activity remaining measured in the time interval from 10 to 20 min. following initiation of the reaction. The activity of thrombin for the controls was $0.0076 \pm 0.0005$ min$^{-1}$.

TABLE 2

Inhibition of Thrombin

| Ex. | Inhibitor | Conc. (nM) | Percent Activity |
|---|---|---|---|
| 72 | Ac—(D)Phe—Pro—boroArg—$C_{10}H_{16}$.HCl | 5 | 1 |
| 73 | Boc—(D)Phe—Pro—boroIrg—$C_{10}H_{16}$.HBr | 5 | 3 |
| 74 | Boc—(D)Phe—Pro—boroArg—$C_{10}H_{16}$.BSA | 5 | 3 |
| 75 | Ac—(D)Phe—Pro—boroArg—OH.HCl | 5 | 3 |
| 76 | H—(D)Phe—Pro—boroIrg—$C_{10}H_{16}$.HBr.HCl | 5 | 4 |
| 77 | H—(D)Phe—Pro—boroArg—$C_{10}H_{16}$.2HCl | 5 | 7 |
| 78 | Boc—(D)Phe—Phe—BoroIrg—$C_{10}H_{16}$Br | 5 | 48 |
| 79 | H—(D)Phe—Phe—boroArg—$C_{10}H_{16}$.2HCl | 10 | 10 |
| 80 | H—Leu—Gly—Leu—Ala—boroArg—$C_{10}H_{16}$.HC.BSA | 10 | 25 |
| 81 | Boc—(D)Phe—Phe—boroArg—$C_{10}H_{16}$.BSA | 10 | 32 |
| 82 | H—Leu—Gly—Leu—Ala—boroIrg—$C_{10}H_{16}$.2HBr | 10 | 37 |
| 83 | Boc—Leu—Gly—Leu—Ala—boroArg—$C_{10}H_{16}$.BSA | 10 | 38 |
| 84 | H—(D)Phe—Phe—boroIrg—$C_{10}H_{16}$.2HBr | 10 | 49 |
| 85 | Bz—Glu(OBu)—Gly—boroArg—$C_{10}H_{16}$.BSA | 10 | 52 |
| 86 | Bz—Glu(OBu—Gly—boroIrg—$C_{10}H_{16}$.HBr | 10 | 59 |
| 87 | Boc—Leu—Gly—Leu—Ala—boroIrg—$C_{10}H_{16}$.HBr | 10 | 66 |
| 88 | Boc—(D)Phe—Pro—boroOrn—$C_{10}H_{16}$.BSA | 100 | 18 |
| 89 | Ac—Ala—Lys(Boc)—boroArg—$C_{10}H_{16}$.BSA | 100 | 18 |
| 90 | Z—Phe—Gly—Gly—boroIrg—$C_{10}H_{16}$.HBr | 100 | 46 |
| 91 | Bz—Glu—Gly—boroArg—$C_{10}H_{16}$.BSA | 100 | 46 |
| 92 | Ac—Ala—Lys(Boc)—boroIrg—$C_{10}H_{16}$.HBr | 100 | 55 |
| 93 | Bz—Pro—Phe—boroArg—OH.HCl | 1000 | 18 |

TABLE 2-continued

Inhibition of Thrombin

| Ex. | Inhibitor | Conc. (nM) | Percent Activity |
|---|---|---|---|
| 94 | Bz—Pro—Phe—boroArg—F | 1000 | 18 |
| 95 | Bz—Pro—Phe—boroIrg—$C_{10}H_{16}$.HBr | 1000 | 21 |
| 96 | Boc—(D)Val—Leu—boroLys—$C_6H_{12}$.HCl | 1000 | 21 |
| 97 | Bz—Pro—Phe—boroArg—$C_{10}H_{16}$.BSA | 1000 | 24 |
| 98 | Boc—Leu—Gly—Leu—Ala—boroOrn—$C_{10}H_{16}$.BSA | 1000 | 24 |
| 99 | Boc—Ala—Phe—(D,L)boroIrg—$C_6H_{12}$.HBr | 1000 | 28 |
| 100 | Bz—Glu—Gly—boroIrg—$C_{10}H_{16}$.HBr | 1000 | 39 |
| 101 | Ac—Ala—Lys—boroArg—$C_{10}H_{16}$.2HCl | 1000 | 45 |
| 102 | Ac—Phe—boroArg—$C_{10}H_{16}$.HCl | 1000 | 53 |
| 103 | Ac—Phe—boroIrg—$C_{10}H_{16}$.HBr | 1000 | 64 |
| 104 | Ac—Ala—Lys—boroIrg—$C_{10}H_{16}$.2HBr | 1000 | 68 |
| 105 | H—Ala—Phe—(D,L)boroIrg—$C_6H_{12}$.2HBr | 10000 | 23 |
| 106 | Boc—Ala—Phe—(D,L)borohomoIrg—$C_6H_{12}$.HBr | 10000 | 32 |
| 107 | Boc—Ala—Phe—(D,L)boroLys—$C_6H_{12}$.HCl | 10000 | 46 |
| 108 | H—Ala—Phe—(D,L)noroHomoIrg—$C_6H_{12}$.2HBr | 10000 | 47 |
| 109 | H—Ala—Phe—D,L)boroLys—$C_6H_{12}$.2HCl | 10000 | 89 |
| 110 | Ac—Phe—boroLys—$C_6H_{12}$.HCl | 10000 | 97 |

EXAMPLES 111-124

Inhibition of Blood Coagulation As Shown by APTT and PT Determination

The effect of protease inhibitors on blood coagulation in vitro was determined by measuring their effects on two different clinical parameters, the activated partial thromboplastin times (APTT) and prothrombin times (PT). Reagents for each of these assays were supplied by General Diagnostics, Jessup MD. Stock solutions of inhibitors were prepared in 25 nM HEPES buffer, pH 7.5, containing 0.10 M sodium chloride. For the APTT assay, the inhibitor solution (0.100 mL) was incubated with normal human plasma (0.100 mL) and automated APTT reagent (0.100 mL). After incubation for 5.0 min at 37°, calcium chloride (0.100 mL) was added and the clotting times, measured in seconds, was determined on a fibrameter. The effects of the varying concentrations of inhibitor on blood clotting times compared with the clotting times of controls run in the absence of inhibitor, are shown in Table 3.

For PT assays, inhibitor solutions (0.100 mL) were incubated with normal human plasma (0.100 mL) for 2 min at 37°. Simplastin reagent (0.200 mL) was then added and clotting times measured as shown in Table 4.

Table 5 provides a summary of the results in Tables 3 and 4, showing the approximate concentrations of inhibitor required to increase the Activated Partial Thromboplastin Times (2×APTT),and the Prothrombin Times (2×PT) two fold.

| Compound Designation In Tables 3-5, 7-10 | Name of Inhibitor |
|---|---|
| A | Boc—(D)Phe—Pro—boroArg—$C_{10}H_{16}$ |
| B | H—(D)Phe—Pro—boroArg—$C_{10}H_{16}$ |
| C | Boc—(D)Phe—Pro—boroIrg—$C_{10}H_{16}$ |
| D | Boc—(D)Phe—Phe—boroIrg—$C_{10}H_{16}$ |
| E | Boc—(D)Phe—Phe—boroArg—$C_{10}H_{16}$ |
| F | Ac—Phe—boroArg—$C_{10}H_{16}$ |
| G | Ac—Phe—boroIrg—$C_{10}H_{16}$ |

TABLE 3

Activated Partial Thromboplastin Times (measured in seconds)

| | Example Number | | | | | | |
|---|---|---|---|---|---|---|---|
| | 111 | 112 | 113 | 114 | 115 | 116 | 117 |
| Conc. | Compound | | | | | | |
| (nM) | A | B | C | D | E | F | G |
| 0 | 35.3 | 32 | 32.8 | 34.7 | 34.7 | 33.7 | 33.8 |
| 50 | | | | 35.8 | 36.8 | 35 | 35.2 |
| 62.5 | | 36.5 | 39.2 | | | | |
| 125 | 36.6 | 44.2 | 46.9 | 45.2 | 40.5 | 35.2 | 36.2 |
| 200 | 40.2 | 71.5 | 67 | 46.2 | 43.6 | 36.7 | 39.3 |
| 250 | 81.2 | 158.7 | 160 | | | | |
| 275 | | | | 60.7 | 52.8 | 44.8 | 58.2 |
| 300 | 113.3 | 169.7 | 197.8 | | | | |
| 350 | 128.7 | 249.7 | 301.8 | 75.7 | 54.8 | 58.2 | 66.7 |
| 550 | | | | 94.8 | 61.3 | 144.2 | 98.4 |

TABLE 4

Prothrombin Times (measured in seconds)

| | Example Number | | | | | | |
|---|---|---|---|---|---|---|---|
| | 118 | 119 | 120 | 121 | 122 | 123 | 124 |
| Conc. | Compound | | | | | | |
| (nM) | A | B | C | D | E | F | G |
| 0 | 15.5 | 15.8 | 14.4 | 15.8 | 16.7 | 15.7 | 15.3 |
| 12.5 | 16.4 | 20.1 | 16.8 | | | | |
| 250 | 17.1 | 22.5 | 20.8 | | | | |
| 500 | 21.5 | 33.8 | 27.2 | 15.7 | 19.8 | | 13.7 |
| 625 | | 46.5 | | | | | |
| 750 | 26.7 | 85.3 | 44 | 17.2 | 22 | | 14.9 |
| 875 | 40.1 | | | | | | |
| 1000 | >200 | >250 | 152.7 | 19.9 | 29.3 | 16.2 | 19.7 |
| 2000 | | | | 23.4 | 39 | 20.8 | 43.6 |
| 4000 | | | | 49.2 | 70.8 | 51.5 | |

TABLE 5

Inhibition of Blood Coagulation

| | Calc. Concentration | |
|---|---|---|
| Compound | 2 × APTT (nM) | 2 × XPT (nM) |
| A | 230 | 800 |
| B | 170 | 460 |
| C | 200 | 650 |
| D | 370 | 1200 |
| E | 375 | 2600 |
| F | 325 | 2500 |
| G | 625 | 1200 |

EXAMPLES 125-127

Inhibition of Blood Coagulation As Shown By TT Determinations

The effect of the protease inhibitor Ac-(D)Phe-Pro-boroArg-OH (Example 8) on blood coagulation in vitro was determined by measuring its effect on thrombin times (TT). A mixture of 0.2 ml of normal rabbit plasma and 0.05 ml of buffer containing the inhibitor at 6 times the desired final concentration was warmed to 37° C. Clotting was initiated by addition of thrombin (0.05 ml at 6 times the final concentration). The thrombin used was purchased from Sigma Chemical Company (No. T-6634, activity 1190 NIH units per mg protein) and prepared in buffer. The buffer employed for both the inhibitor and the thrombin was 0.1 M Tris buffer (12.10 g/L), containing 0.154 M NaCl (8.84 g/L) and 2.5 mg/ml bovine serum albumin, pH 7.4. The clotting times, measured in seconds, were determined using a fibrometer. The effects of the inhibitor on blood clotting times compared with the blood clotting times of controls run in the absence of inhibitors, are shown in Table 6. Values represent the average of at least three determinations. If clotting did not occur within 300 seconds, the reaction was terminated.

TABLE 6

Thrombin Times

| Ex. | Thrombin Conc. (μ/ml) | Inhibitor Conc. (nM) | Thrombin Times* |
|---|---|---|---|
| — | 0.75 | 0 | >300 |
| — | 0.83 | 0 | 226.9 ± 14.8 |
| — | 1 | 0 | 147.2 ± 9.1 |
| — | 1.2 | 0 | 121.1 ± 0.8 |
| — | 2 | 0 | 51.8 ± 0.6 |
| — | 3 | 0 | 40.0 ± 1.9 |
| — | 4 | 0 | 24.4 ± 0.3 |
| 125 | 4 | 150 | >300 |
| 126 | 4 | 100 | 62.4 ± 7.2 |
| 127 | 4 | 50 | 32.7 ± 0.8 |

*the mean time needed for clotting, measured in seconds, ± the standard deviation

EXAMPLES 128-132

Stability of Inhibitors in Human Plasma As Measured By APTT

The stability of inhibitors in plasma was determined by their ability to inhibit blood coagulation. First, a stock solutions (1.0 μM) of the inhibitors to be tested in 25 mM HEPES buffer, pH 7.5, containing 0.10 M sodium chloride were diluted 50% with normal human plasma. The mixtures were made at 0°, then aliquots (0.200 mL) were removed and incubated for 2 min at 37°. An equal volume of automated APTT reagent was added and clotting times were measured as described in Examples 111-117. The final concentration of inhibitor during the clotting assays was 250 nM. The incubation times (shown in hours) and clotting time (measured in seconds) for individual inhibitors are shown in Table 7. Values for compounds E and F were determined simultaneously with the Control. Values for compounds A, B and C were obtained on a different day.

TABLE 7

Stability of Inhibitors in Human Plasma

| | | Example Number | | | | |
|---|---|---|---|---|---|---|
| | | 128 | 129 | 130 | 131 | 132 |
| | | Compound | | | | |
| Incubation Time (h) | Control | F | E | A | B | C |
| | | Clotting Time (sec) | | | | |
| 0 | 41.5 | 76.3 | 63.2 | 81.2 | 152.2 | 203.2 |
| 0.5 | 42.7 | 76.4 | 73.2 | 84.7 | 157.7 | 207.2 |
| 1 | 42.7 | 76.7 | 66.2 | 79.7 | 163.7 | 214.2 |
| 2 | 42.7 | 79.6 | 67.7 | 86.7 | 152.8 | 203.7 |
| 3 | 44.8 | 77.8 | 61.7 | | | |
| 4 | 44.2 | 81.8 | 58.2 | 98.2 | 157.7 | 209.7 |
| 5 | 45.7 | 80.8 | 61.3 | | | |
| 6 | 45.2 | 79.3 | 57.3 | | | |
| 24 | 35.2 | 73.9 | 64.7 | 92.2 | 109.3 | 248.7 |
| 48 | 47.2 | 49.3 | 58.7 | | | |

EXAMPLES 133-136

Stability of Inhibitors in Buffer

Inhibitors, each at a concentration of 1.0 μM, were incubated at room temperature in 0.20 M sodium phosphate buffer, pH 7.5, containing 0.20 M sodium chloride and 0.10% PEG. Aliquots (4.0 μL) were removed and assayed in the thrombin assay as described in Examples 72-110. The percent of thrombin activity remaining after incubation and the lengths of time the inhibitors were in the sodium phosphate buffer is reported in Table 8. With inhibitors A and C, there is little loss of inhibitor activity. Inhibitor B loses its biological activity over a period of an hour.

TABLE 8

Stability of Inhibitors in Buffer

| Example No. | Compound | Percent Thrombin activity | | |
|---|---|---|---|---|
| | | 0 hr | 6.5 hr | 24 hr |
| 133 | A | 3.3 | 1.6 | 0.8 |
| 134 | C | 3.0 | | 0.9 |
| 135 | C | 65 | | 77 |
| | | 0 hr | 0.5 hr | 1 hr |
| 136 | B | 2.0 | 15 | 100 |

EXAMPLES 137-142

Inhibition of Blood Coagulation Following In Vivo Oral Dosing

Male rats (Sprague Dawley CD Rats, 130-140 g, supplied by Charles River Labs, Inc., Wilmington, MA) were anesthetized with sodium pentobarbital (50 mg/kg, i.p.). A midline incision was made on the ventral surface of the neck, and a polyethylene catheter was inserted in one of the carotid arteries and exteriorized at the back of the neck. After recovery from anesthesia, control blood samples were taken from the carotid artery catheter, anticoagulated with sodium citrate, and centrifuged (2000×g, 10 minutes). Plasma was transferred to plastic tubes and kept on ice until it was assayed. Thrombin times were measured using a fibrometer, as described in Examples 125-127.

Rats were given either the protease inhibitor Ac-(D)Phe-Pro-boroArg-OH in a vehicle, or the vehicle alone, by oral gavage in a volume of less than 4 ml. The vehicle employed was 5% dimethylsulfoxide in saline. Blood samples were taken at various times after oral dosing and assayed as described above. The results, shown in clotting times in seconds, are given in Table 9, below. When clotting time exceeded 300 seconds, it is reported below as >300. The remaining data show the mean time needed for clotting, measured in seconds, ±the standard deviation.

TABLE 9

Inhibition of Blood Coagulation Following In Vivo Oral Dosing

| Ex. | Time (hr) | Control | Inhibitor Concentration | | |
|---|---|---|---|---|---|
| | | | 1 mg | 2 mg | 10 mg |
| 137 | .5 | 68 ± 18 | >300 | >300 | >300 |
| 138 | 1 | 52 ± 26 | >300 | ND* | >300 |
| 139 | 2 | 55 ± 11 | >300 | ND* | >300 |
| 140 | 3 | 34 ± 12 | >300 | ND* | >300 |
| 141 | 4 | 41 | 47 ± 4 | 54 ± 29 | ND* |
| 142 | 6 | 50 | 46 ± 3 | 44 ± 4 | ND* |

*ND = not determined

EXAMPLE 143

In Vivo Inhibition of Blood Coagulation Following Oral Dosing

To further demonstrate the ability of this compound to inhibit blood coagulation in vivo, rats were anesthetized with sodium pentobarbital (50 mg/kg, i.p.), a jugular vein catheter was inserted, and the incision was closed. After recovery from anesthesia, rats were treated orally with either 5 mg/kg of the protease inhibitor Ac-(D)Phe-Pro-boroArg-OH dissolved in water, or an equal volume of water. Thirty to sixty minutes later, all rats received an infusion of 500 units/kg thrombin over a period of one minute. All fourteen rats given only water died within ten minutes of the thrombin infusion. In contrast only 8 out of 17 rats treated with the inhibitor-containing water died within ten minutes, and the remainder survived one hour, at which time they were euthanized.

EXAMPLES 144-162

In Vivo Inhibition of Blood Coagulation Following Oral, Colonic and Rectal Administration

General Procedures

Male Lewis rats weighing between 300-350 g were anesthetized with sodium pentobarbitol (50 mg/kg, i.p.) and the jugular vein was cannulated using a silastic tubing attached to a polyethylene 50 tubing. The tubing was exteriorized at the back of the neck and attached to a syringe through a stop cock. Blood samples (0.5 ml) were withdrawn before and at different time intervals after dosing with the protease inhibitor Ac-(D)Phe-Pro-boroArg-OH, into the syringe that was flushed with citrate buffer prior to each collection. The blood samples were then transferred into vacutainers containing citrate buffer. Also, after each collection the cannula was flushed with saline. The blood samples were then centrifuged immediately (2500 rpm for 15 min) and 0.2 ml of the plasma samples were used for clotting time measurements. The clotting time measurements were carried out using a fibrometer as follows. First, plasma (0.2 ml) was placed in a fibro cup, and pH 7.4 Tris buffer (50 microliters) was added. The plasma buffer solution was incubated at 37° C. for 1 min, 50 microters of a 24 μ/ml thrombin solution in Tris buffer was then added, and clotting time in seconds was measured. When clotting time exceeded 300 seconds, it is reported below as >300.

Oral dosing

The jugular vein-cannulated rats were allowed to recover from anesthesia before they were dosed orally. The protease inhibitor Ac-(D)Phe-Pro-boroArg—OH aqueous solution, consisting of 3 mg of inhibitor per kg weight of rat (approximately 1 mg/rat) in a volume of 0.75 ml of water per kg of rat, was administered by gavage. The results are reported in Table 10, below.

Colonic administration

A 3 cm incision was made in the abdomen of the jugular vein-cannulated rats while they were still under anesthesia. The colon was located and was tied off at both the beginning and the end. The protease inhibitor Ac-(D)Phe-Pro-boroArg—OH aqueous solution, consisting of 3 mg of inhibitor per kg weight of rat (approximately 1 mg/rat) in a volume of 1 ml of water per kg weight of rat, was injected at the beginning into the colon cavity. The incision was closed using wound clips. The results are reported in Table 11, below.

Rectal administration

The procedure for rectal administration in the jugular vein-cannulated rats was as described by Kamiya et al., J. Pharm. Sci., 71: 621 (1982). In brief, a device was made consisting of a 0.89 cm and a 0.71 cm silicon rubber septa connected by a 2 cm length of wire. This device was inserted into the rectum of the rat, the large septum first, and glued to the annus using suitable glue. Dosing was accomplished by injection through the exposed septum. The rectal dose was 3 mg of of the protease inhibitor Ac-(D)Phe-Pro-boroArg—OH per kg weight of rat (approximately 1 mg/rat) in a volume of 0.6 ml of water per kg of rat. The results are reported in Table 12, below.

TABLE 10

In Vivo Inhibition of Blood Coagulation of Following Oral Administration

| Ex. | Time (hr) | Control* | Inhibitor** |
|---|---|---|---|
| 144 | 0.00 | 49.7 | 57.3 |
| 145 | 0.25 | 67.4 | >300 |
| 146 | 0.50 | 51.8 | >300 |
| 147 | 1.00 | 43.6 | >300 |
| 148 | 2.00 | 42.5 | >300 |
| 149 | 3.00 | 58.4 | >300 |
| 150 | 4.00 | 42.7 | >300 |

*data represents the average for 2 rats
**data represents the mean for 3 rats

TABLE 11

In Vivo Inhibition of Blood Coagulation Following Colonic Administration

| Ex. | Time (hr) | Control* | Inhibitor** |
|---|---|---|---|
| 151 | 0.0 | 59.9 | 59.4 |
| 152 | 0.5 | 42.7 | >300 |
| 153 | 1.0 | 42.7 | >300 |
| 154 | 2.0 | 52.1 | >300 |
| 155 | 4.0 | 54.2 | >300 |
| 156 | 5.0 | 57.9 | >300 |

*data represnts the average for 2 rats
**data represnts the mean for 3 rats

TABLE 12

In Vivo Inhibition of Blood Coagulation Following Rectal Administration

| Ex. | Time (hr) | Control* | Inhibitor** |
|---|---|---|---|
| 157 | 0 | 53.9 | 66.4 |
| 158 | 0.25 | 52.3 | >300 |
| 159 | 0.5 | 43.1 | >300 |
| 160 | 1.0 | 52.7 | >300 |
| 161 | 2.0 | 42.5 | >300 |

TABLE 12-continued

In Vivo Inhibition of
Blood Coagulation Following Rectal Administration

| Ex. | Time (hr) | Control* | Inhibitor** |
|---|---|---|---|
| 162 | 4.0 | 75.6 | >300 |

*data obtained from 1 rat
**data represnts the mean for 3 rats

EXAMPLES 163-168

In Vivo Inhibition of Croton Oil Induced Inflammation

Two solutions were prepared, the first consisting of 5% croton oil, a known inflammatory agent, in an acetone carrier (Croton Solution) and the second consisting of 5% croton oil in an acetone carrier to which 10 mg/mL of a compound of the invention was added (Compound Solution). The Croton Solution (10 μL), or alternatively the Compound Solution (10 μL), was applied to the right ear of each animal (Sprague Dawley CD Rats, 130–140 g, supplied by Charles River Labs, Inc., Wilmington, MA). The acetone carrier alone (Acetone (10 μL) was applied to the left ear of each animal. At 1 h following treatment, the animals were sacrificed, their ears removed and ¼ inch diameter disks punched out and weighed. Swelling the difference in weight between the Croton Solution treated right ear and the Acetone Solution treated left ear. The results are compared with indomethacin, a known non-steroid anti-inflammatory (Indomethacin Solution),which was prepared and applied in a manner substantially identical to the Compound Solution. Mean data are shown in Table 13 for Compound F, Ac-Phe-boroArg-$C_{10}H_{14}$. The term "dose" as used below, indicates the amount of active anti-inflammatory ingredient in μg (Compounds A, C, D, E, F or G, or Indomethacin, as the case may be) in the solution applied to each right ear, and "n" indicates the number applied to each right ear, and "n" indicates the number of rats used in each test. "SE" denotes standard error. Examples 164–168 in Table 14 show the anti-inflammatory activity for Compounds A, C, D, E, F and G which were run under essentially the same conditions (dose=100 μg).

TABLE 13

Inhibition of Croton Oil Induced Inflamation
Example 163

| Soln. | Dose Right ear (μg/ear) | Mean Right ear Wt. (mg) | Mean Left ear Wt. (mg) | Mean Swelling (mg ± SE) | Percent Inhibition | n |
|---|---|---|---|---|---|---|
| Croton | 0 | 27.4 | 16.3 | 11.1 ± 1.5 | 0 | 8 |
| Indometh. | 100 | 20.6 | 15.6 | 5.0 ± 2.8 | 55 | 8 |
| Cmpd. F | 100 | 18.9 | 16.6 | 2.3 ± 0.7 | 79 | 8 |

TABLE 14

Inhibition of Croton Oil Induced Inflammation

| Example No. | Compound | Percent Inhibition |
|---|---|---|
| 164 | G | 69 |
| 165 | E | 82 |
| 166 | D | 93 |
| 167 | A | 59 |
| 168 | C | 76 |

What is claimed is:
1. A compound of the formula

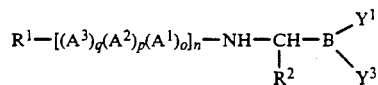

[FORMULA I]

wherein
$Y^1$ and $Y^2$, independently, are —OH or F or, taken together, form a moiety derived from a dihydroxy compound having at least two hydroxy groups separated by at least two connecting atoms in a chain or ring, said chain or ring comprising 1 to about 20 carbon atoms and, optionally, a heteroatom which can be N, S, or O;

$R^2$ is a substituted alkyl selected from the group consisting of —$(CH_2)_z$—X, —$CH(CH_3)$—$(CH_2)_2$—X, —$CH_2CH(CH_3)$—$CH_2$—X, —$(CH_2)_2$—$CH(CH_2)$—X, and —$(CH_2)_2$—$CH(CH_3)_2$—X, where X is —$NH_2$, —NH—C(NH)—$NH_2$ or —S—C(NH)—$NH_2$, and z is 3 to 5;

n, o, p, and q are, independently, either 1 or 0;

$A^1$, $A^2$ and $A^3$, independently, are amino acids of L- or D-configuration selected from the group consisting of Ala, Arg, Asn, Asp, Cys, Gln, Glu, Gly, His, Ile, Leu, Lys, Met, Phe, Pro, Ser, Thr, Trp, Tyr and Val; and $R^1$ is H or an N-terminal protecting group;

or a physiologically acceptable salt thereof.

2. A compound according to claim 1 wherein $A^1$ is an amino acid of L- or D-configuration selected from the group consisting of Lys, Phe, Pro, Ala, Leu, Gly, Glu, Val, Thr, Ile, Met, Tyr, Trp, Arg, Asp, Asn and Gln.

3. A compound according to claim 2 wherein $A^1$ is an amino acid of L- or D-configuration selected from the group consisting of Lys, Phe, Pro, Ala, Leu, Gly, Glu, Val and Thr.

4. A compound according to claim 1 wherein $A^2$ is an amino acid of D-configuration.

5. A compound according to claim 4 wherein $A^2$ is Phe.

6. A compound according to claim 1 wherein $A^2$ is an amino acid of L- or D-configuration selected from the group consisting of Phe, Ala, Leu, Pro, Glu and 7. A compound according to claim 1 wherein $R^2$ is a substituted alkyl selected from the group consisting of —$(CH_2)_z$—X.

8. A compound according to claim 7 wherein z is 3 to 4.

9. A compound according to claim 7 wherein $R^2$ is selected from the group consisting of 3-guanidino-propyl, 3-amino-propyl and 4-amino-butyl.

10. A compound according to claim 9 wherein is 3-guanidino-propyl.

11. The compound according to claim 1 which is Ac-(D) Phe-Pro-boroArg-OH.

12. A compound of claim 1 wherein the N-terminal protecting group is an acyl or a sulfonyl group comprised of 1 to about 20 carbon atoms.

13. A compound of claim 12 wherein $A^1$ is an amino acid of L- or D-configuration selected from the group consisting of Lys, Phe, Pro, Ala, Leu, Gly, Glu, Val, Thr, Ile, Met, Tyr, Trp, Arg, Asp, Asn, and Gln.

14. A compound of claim 13 wherein $A^1$ is an amino acid of L- or D-configuration selected from the group consisting of Lys, Phe, Pro, Ala, Leu, Gly, Val, and Thr.

15. A compound of claim 12 wherein $A^2$ is an amino acid of D-configuration.

16. A compound of claim 15 wherein $A^2$ is Phe.

17. A compound of claim 12 wherein $A^2$ is an amino acid of L- or D-configuration selected from the group consisting of Phe, Ala, Leu, Pro, Glu, and Gly.

18. A compound of claim 12 wherein $R^2$ is a substituted alkyl selected from the group consisting of —$(CH_2)_z$—X.

19. A compound of claim 18 wherein z is 3 to 4.

20. A compound of claim 18 wherein $R^2$ is selected from the group consisting of 3-guanidino-propyl, 3-amino-propyl, and 4-amino-butyl.

21. A composition for inhibiting a trypsin-like serine protease in a mammal comprising an effective amount of a compound of claim 1 and a physiologically acceptable carrier or diluent.

22. A composition for inhibiting a trypsin-like serine protease in a mammal comprising an effective amount of a compound of claim 2 and a physiologically acceptable carrier or diluent.

23. A composition comprising an effective amount of the compound of claim 11 and a physiologically acceptable carrier or diluent.

24. A composition for inhibiting thrombin in a mammal comprising an effective amount of a compound of claim 1 and a physiologically acceptable carrier or diluent.

25. A composition for inhibiting thrombin in a mammal comprising an effective amount of a compound of claim 2 and a physiologically acceptable carrier or diluent.

26. A composition for inhibiting a trypsin-like serine protease in a mammal comprising an effective amount of a compound of claim 12 and a physiologically acceptable carrier or diluent.

27. A composition for inhibiting thrombin in a mammal comprising an effective amount of a compound, of claim 11 and a physiologically acceptable carrier or diluent.

28. A composition for inhibiting plasma kallikrein in a mammal comprising an effective amount of a compound of claim 1 and a physiologically acceptable carrier or diluent.

29. A composition for inhibiting plasma kallikrein in a mammal comprising an effective amount of a compound of claim 2 and a physiologically acceptable carrier or diluent.

30. A composition for inhibiting plasmin in a mammal comprising an effective amount of a compound of claim 1 and a physiologically acceptable carrier or diluent.

31. A composition for inhibiting plasmin in a mammal comprising an effective amount of a compound of claim 2 and a physiologically acceptable carrier or diluent.

32. A composition for treating blood coagulation in a mammal comprising an effective amount of a compound of claim 1 and a physiologically acceptable carrier or diluent.

33. A composition for treating blood coagulation in a mammal comprising an effective amount of a compound of claim 2 and a physiologically acceptable carrier or diluent.

34. A composition for treating blood coagulation in a mammal comprising an effective amount of a compound of claim 11 and a physiologically acceptable carrier or diluent.

35. A composition for treating inflammation in a mammal comprising an effective amount of a compound of claim 1 and a physiologically acceptable carrier or diluent.

36. A composition for treating inflammation in a mammal comprising an effective amount of a compound of claim 2 and a physiologically acceptable carrier or diluent.

37. A method of inhibiting a trypsin-like serine protease in a mammal comprising administering to the mammal an effective amount of a compound of claim 1.

38. A method of inhibiting a trypsin-like serine protease in a mammal comprising administering to the mammal an effective amount of a compound of claim 2.

39. A method of inhibiting a trypsin-like serine protease in a mammal comprising administering to the mammal an effective amount of the compound of claim 11.

40. A method of claim 37 wherein the trypsin-like serine protease is thrombin.

41. A method of claim 38 wherein the trypsin-like serine protease is thrombin.

42. A method of claim 39 wherein the trypsin-like serine protease is thrombin.

43. A method of claim 37 wherein the trypsin-like serine protease is plasma kallikrein.

44. A method of claim 38 wherein the trypsin-like serine protease is plasma kallikrein.

45. A method of claim 37 wherein the trypsin-like serine protease is plasmin.

46. A method of claim 38 wherein the trypsin-like serine protease is plasmin.

47. A method of treating blood coagulation in a mammal comprising administering to the mammal an effective amount of a compound of claim 1.

48. A method of treating blood coagulation in a mammal comprising administering to the mammal an effective amount of a compound of claim 2.

49. A method of treating blood coagulation in a mammal comprising administering to the mammal an effective amount of the compound of claim 11.

50. A method of treating inflammation in a mammal comprising administering tho the mammal an effective amount of a compound of claim 1.

51. A method of treating inflammation in a mammal comprising administering to the mammal an effective amount of a compound of claim 2.

* * * * *

UNITED STATES PATENT AND TRADEMARK OFFICE
CERTIFICATE OF CORRECTION

PATENT NO. : 5,187,157

DATED : February 16, 1993

INVENTOR(S) : Charles A. Kettner and Ashokkumar B. Shenvi

Page 1 of 2

It is certified that error appears in the above-indentified patent and that said Letters Patent is hereby corrected as shown below:

At column 3, line 31, under the definition of $R^2$, the last member of the Markush group of substituents "$-(CH_2)_2-CH(CH_3)_2-X$" (the second occurence) should be deleted and replaced with -- $-(CH_2)_2-C(CH_3)_2-X$ --.

At column 4, line 2, under the definition of $R^3$, the last member of the Markush group of substituents "$-(CH_2)_2-CH(CH_3)_2-W^1$" (the second occurence) should be deleted and replaced with -- $-(CH_2)_2-C(CH_3)_2-W^1$ --.

At column 4, line 18, under the definition of $R^4$, the last member of the Markush group of substituents "$-(CH_2)_2-CH(CH_3)_2-W^2$" (the second occurence) should be deleted and replaced with -- $-(CH_2)_2-C(CH_3)_2-W^2$ --.

At column 8, line 66, under the definition of $R^3$, the last member of the Markush group of substituents "$-(CH_2)_2-CH(CH_3)_2-W^1$" (the second occurence) should be deleted and replaced with -- $-(CH_2)_2-C(CH_3)_2-W^1$ --.

At column 9, line 17, under the definition of $R^4$, the last member of the Markush group of substituents "$-(CH_2)_2-CH(CH_3)_2-W^2$" (the second occurence) should be deleted and replaced with -- $-(CH_2)_2-C(CH_3)_2-W^2$ --.

UNITED STATES PATENT AND TRADEMARK OFFICE
CERTIFICATE OF CORRECTION

PATENT NO. : 5,187,157
DATED : February 16, 1993
INVENTOR(S) : Charles A. Kettner and Ashokkumar B. Shenvi It is certified that error appears in the above-indentified patent and that said Letters Patent is hereby corrected as shown below:

At column 3, lines 15-20, in Formula I, delete "$Y^3$" and insert --$Y^2$--.

At column 50, lines 2-7, in Formula I, delete "$Y^3$" and insert --$Y^2$--.

At column 50, line 19, under the definition of $R^2$, the last member of the Markush group of substituents "$-(CH_2)_2-CH(CH_3)_2-X$" (the second occurence) should be deleted and replaced with --    $-(CH_2)_2-C(CH_3)_2-X$    --.

Signed and Sealed this

Twenty-sixth Day of April, 1994

Attest:

BRUCE LEHMAN

*Attesting Officer*    *Commissioner of Patents and Trademarks*